(12) United States Patent
Bonutti

(10) Patent No.: US 6,171,299 B1
(45) Date of Patent: *Jan. 9, 2001

(54) METHOD OF PROVIDING SURGICAL ACCESS THROUGH AN INCISION

(75) Inventor: Peter M. Bonutti, Effingham, IL (US)

(73) Assignee: General Surgical Innovations, Inc., Norwalk, CT (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/462,420

(22) Filed: Jun. 5, 1995

Related U.S. Application Data

(60) Division of application No. 08/195,337, filed on Feb. 14, 1994, now Pat. No. 5,514,153, which is a continuation-in-part of application No. 07/792,730, filed on Nov. 15, 1991, now Pat. No. 5,295,994, and a continuation-in-part of application No. 08/054,416, filed on Apr. 28, 1993, now abandoned, which is a division of application No. 07/487,645, filed on Mar. 2, 1990, now Pat. No. 5,331,975.

(51) Int. Cl.[7] .................................................. A61B 17/00
(52) U.S. Cl. .................. 606/1; 604/164.03; 604/164.04; 604/167.03; 128/898
(58) Field of Search ..................................... 606/192, 194, 606/185, 1; 600/115, 207; 604/164, 99.04, 101.01, 164.03, 164.02, 167.02, 167.01, 167.03, 167.06, 164.04; 128/898

(56) References Cited

U.S. PATENT DOCUMENTS

| | | | |
|---|---|---|---|
| 3,970,089 | 7/1976 | Saice ..................................... | 128/348 |
| 4,177,814 | 12/1979 | Knepshield et al. .................. | 128/348 |
| 4,240,433 | * 12/1980 | Bordow . | |
| 4,545,374 | * 10/1985 | Jacobson . | |
| 4,555,242 | 11/1985 | Saudagar ............................... | 604/96 |
| 4,630,609 | * 12/1986 | Chin ..................................... | 606/194 |
| 4,796,629 | 1/1989 | Grayzel ................................ | 128/344 |
| 4,932,959 | * 6/1990 | Horzewski et al. .................. | 606/194 |
| 5,071,411 | 12/1991 | Hillstead .............................. | 604/246 |
| 5,104,383 | 4/1992 | Shichman ............................. | 604/167 |
| 5,143,093 | * 9/1992 | Sahota .................................. | 606/194 |
| 5,158,553 | * 10/1992 | Berry et al. .......................... | 604/248 |
| 5,159,921 | * 11/1992 | Hoover ................................. | 600/207 |
| 5,197,955 | 3/1993 | Stephens et al. .................... | 604/167 |
| 5,226,426 | * 7/1993 | Yoon .............................. | 606/185 X |
| 5,445,615 | * 8/1995 | Yoon .................................. | 604/99.04 |

FOREIGN PATENT DOCUMENTS

0418147 * 3/1991 (EP) ..................................... 600/115

* cited by examiner

Primary Examiner—Michael H. Thaler

(57) ABSTRACT

An active cannula or sleeve which does more than merely maintain a channel or passage is usable to create and/or enlarge a channel or passage, to position a scope or instrument, to move or locate tissue, etc. The cannula can vary in size or shape as needed, intraoperatively. Because a cannula of the present invention is expandable, the surgeon can make a small relatively small incision, stretch the tissue with the expandable cannula, contract the cannula and remove it, allowing the skin to come back to its unstretched condition. Thus, a smaller incision can be made to fit the same size instrument. This results in less trauma and scarring and an easier operation. The cannulas are or can assume such a non-circular shape, to fit into a natural skin opening and cause less trauma. The devices can be used to seal off a space; to expand an existing space or a potential space for working or visualization; to move tissue (for example, to stretch an incision) or to protect it.

35 Claims, 24 Drawing Sheets

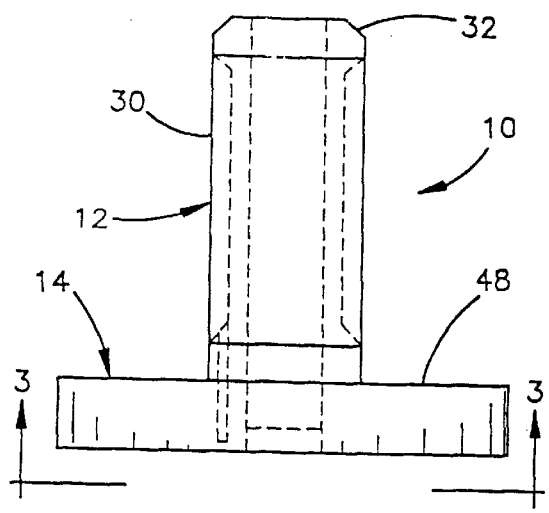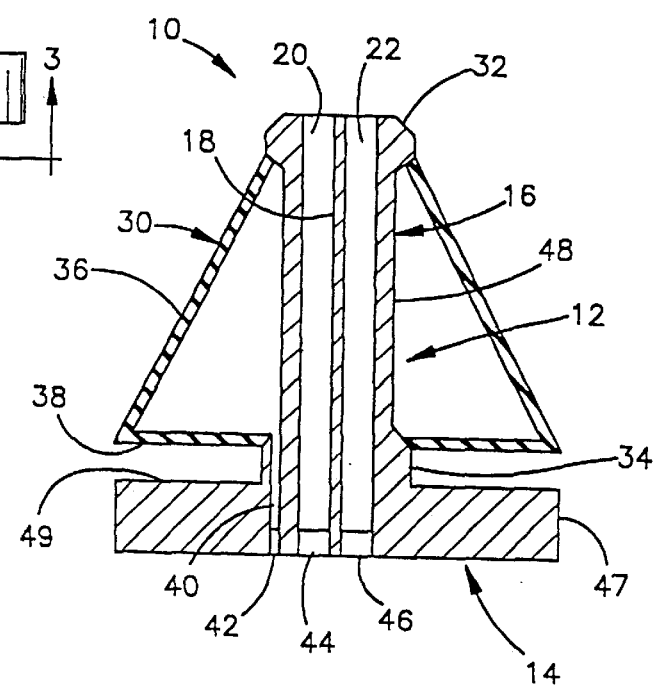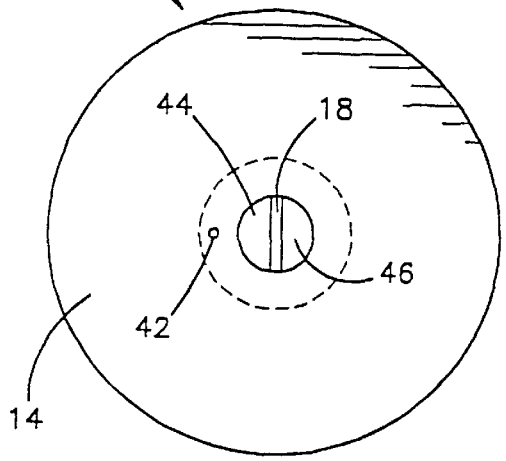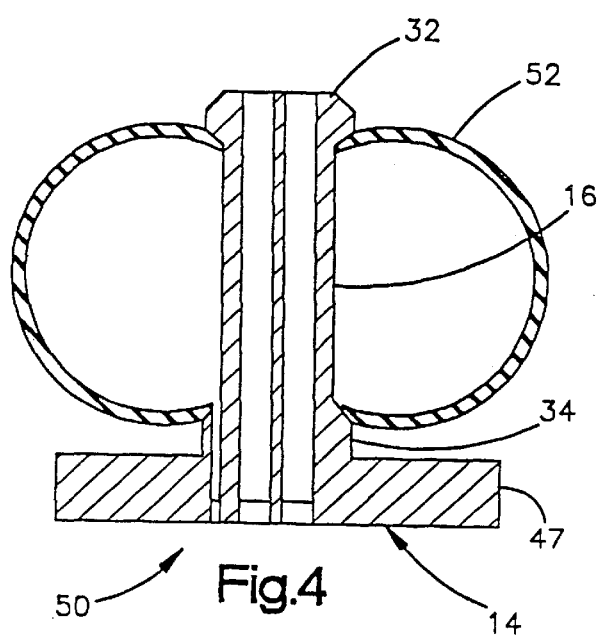
Fig.1
Fig.2
Fig.3
Fig.4

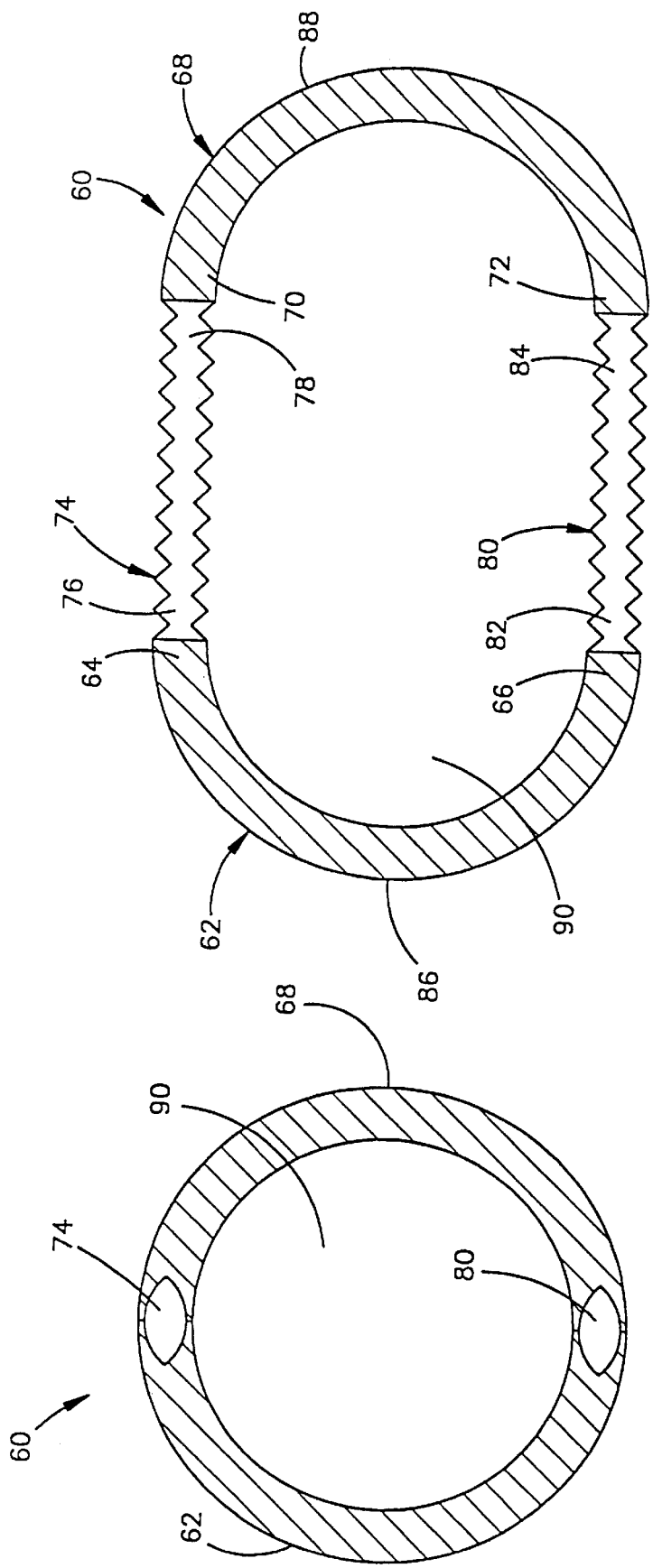

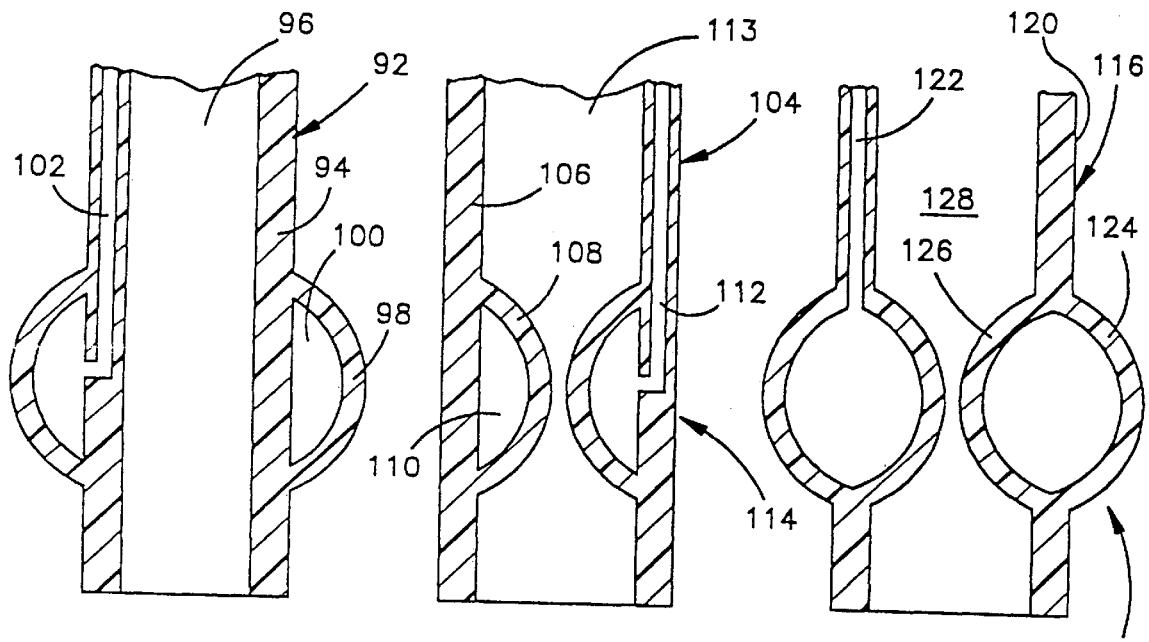
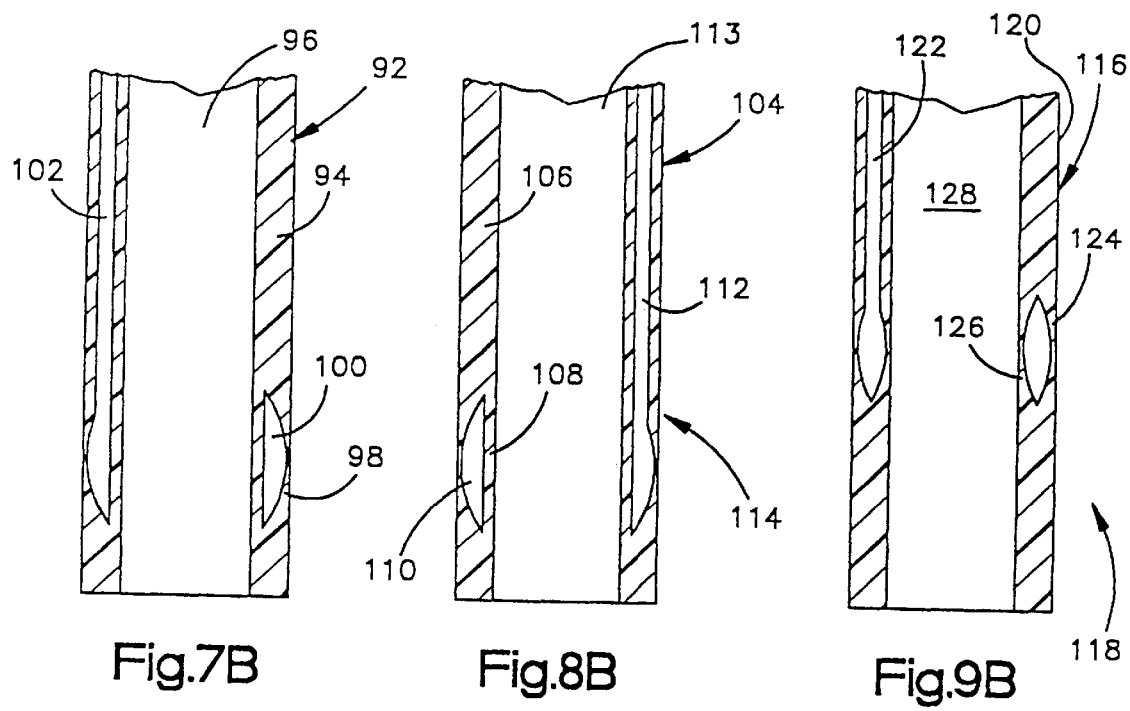
Fig.7A  Fig.8A  Fig.9A
Fig.7B  Fig.8B  Fig.9B

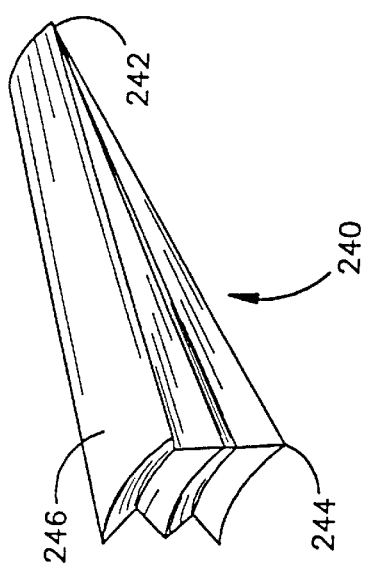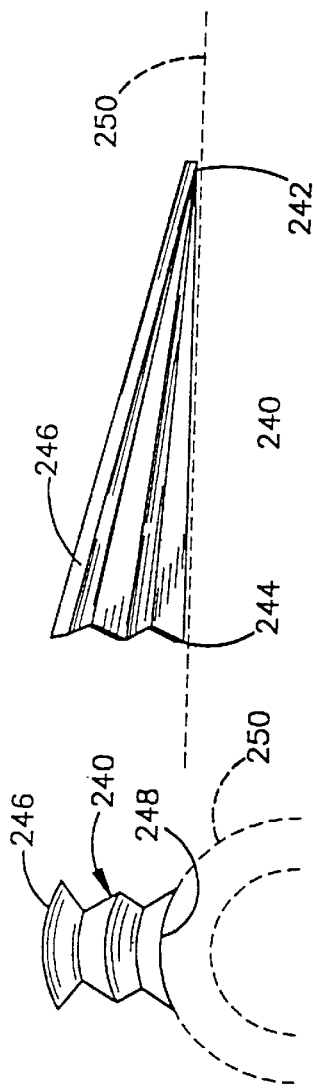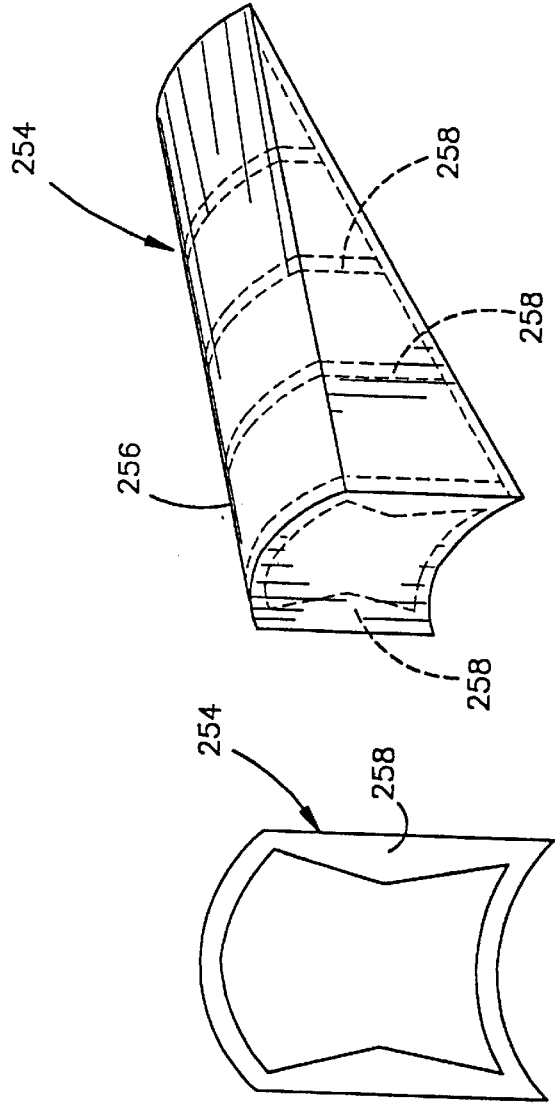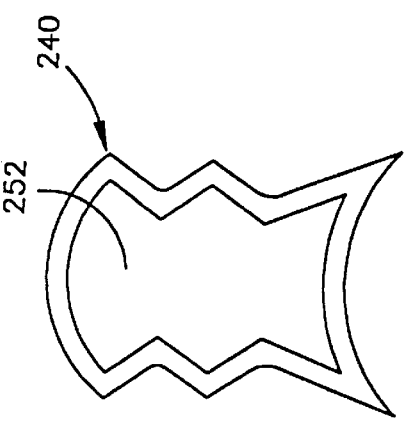

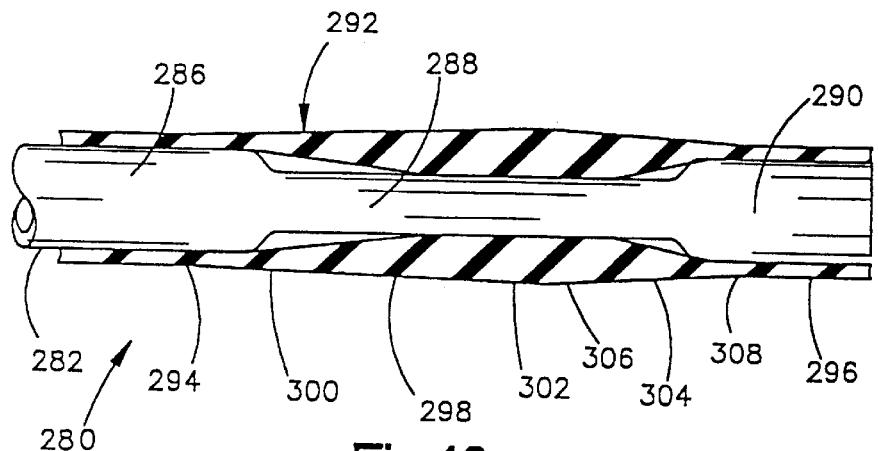
Fig.46
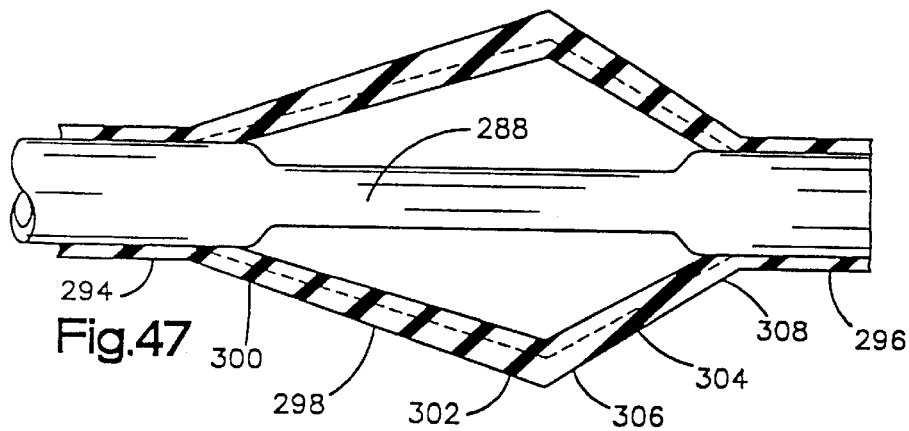
Fig.47
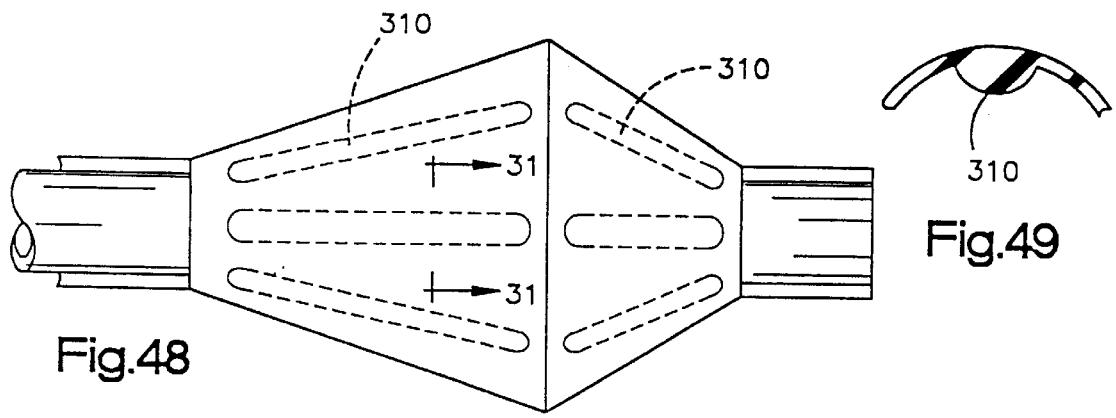
Fig.48
Fig.49

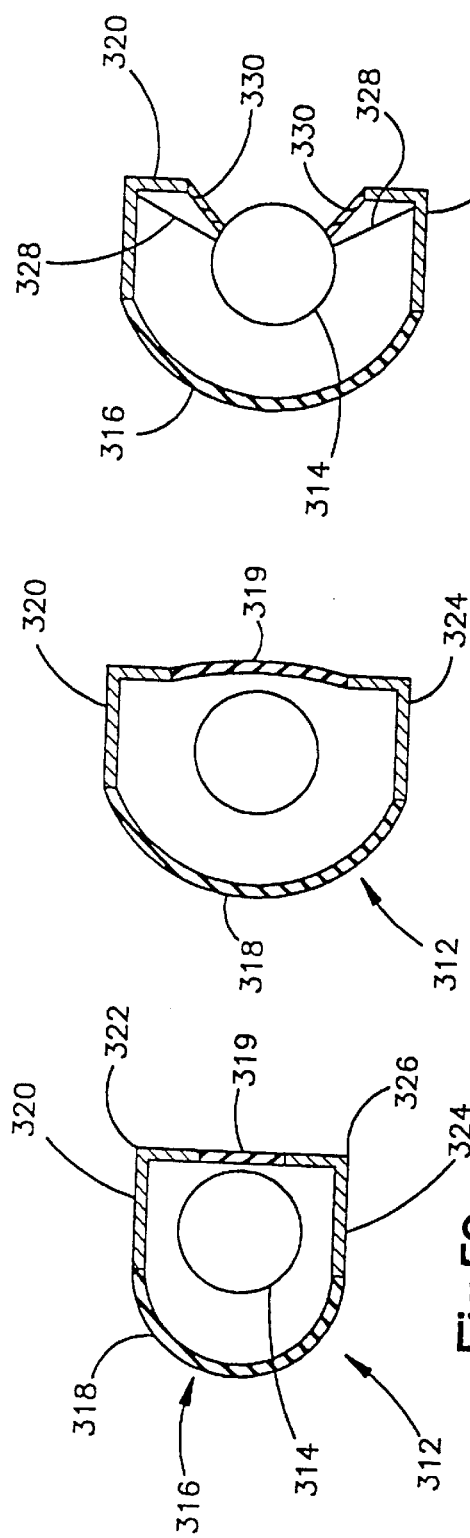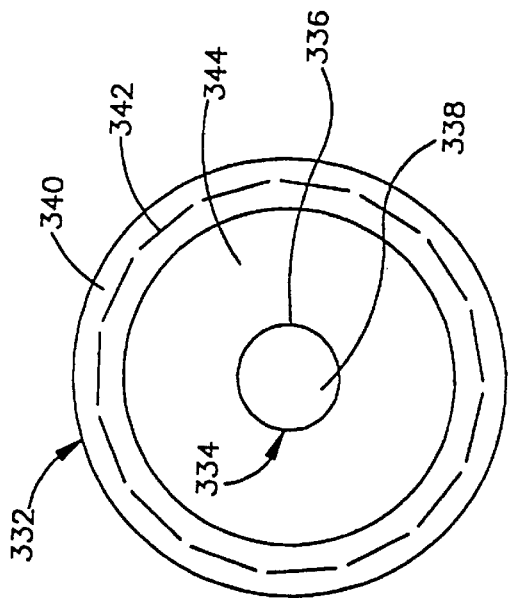

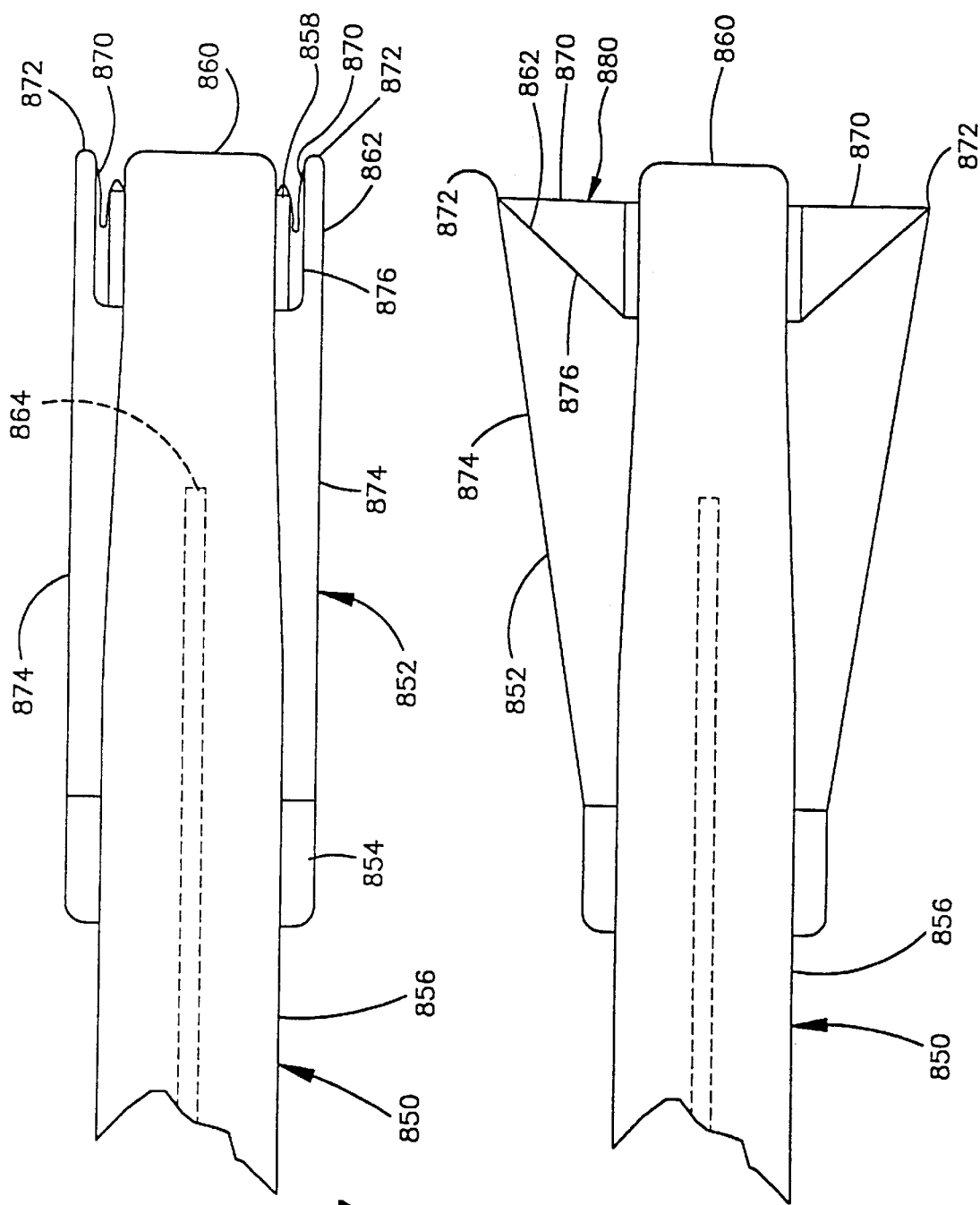

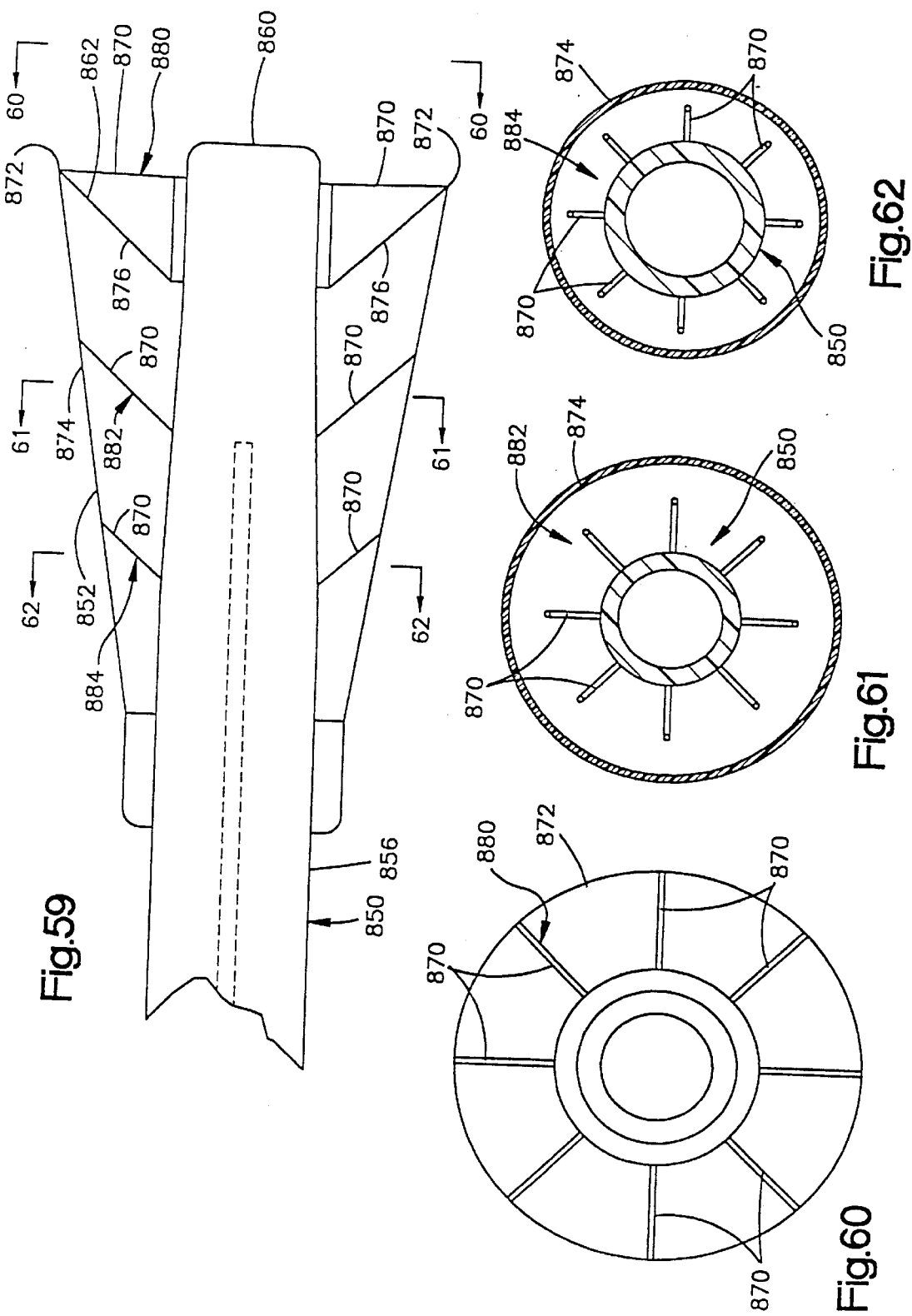

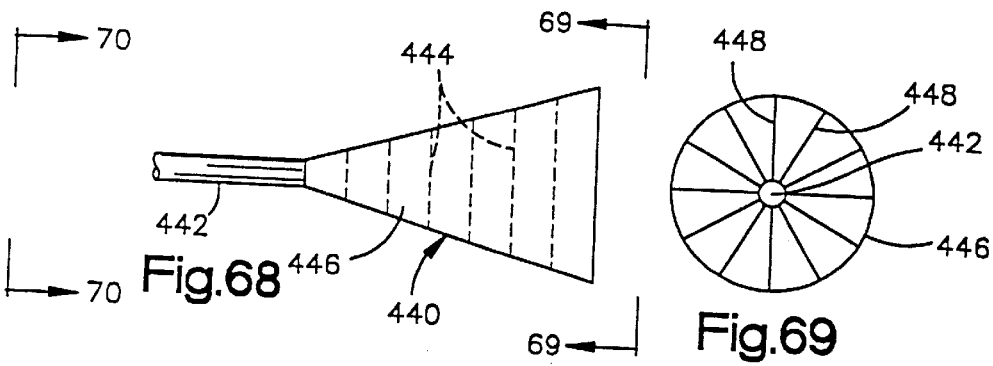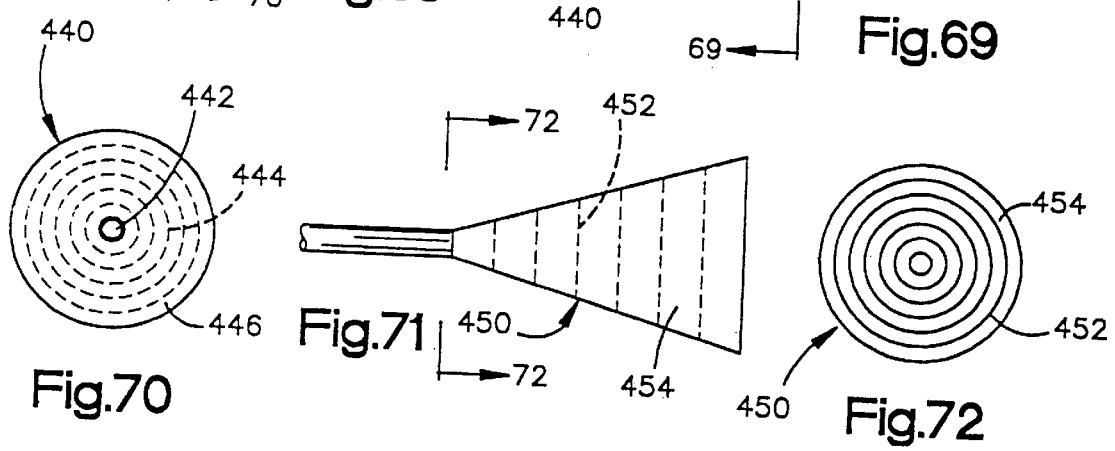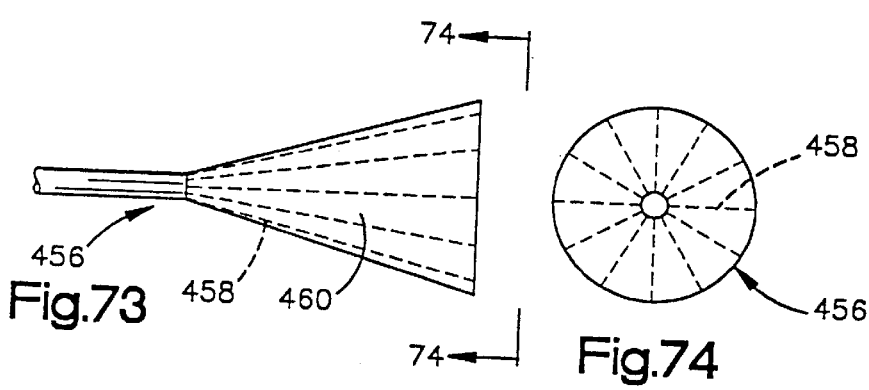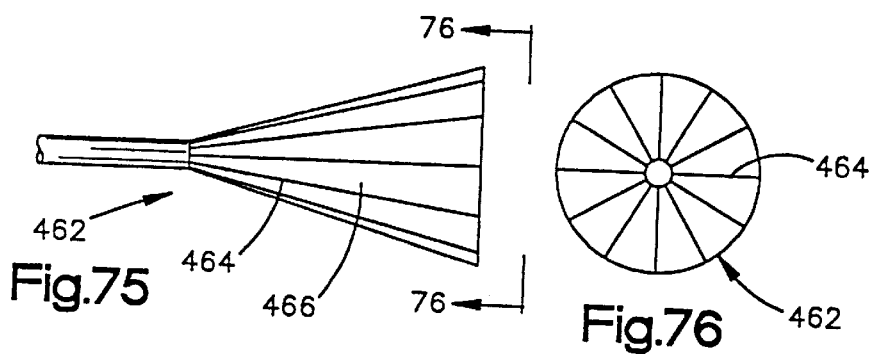

METHOD OF PROVIDING SURGICAL ACCESS THROUGH AN INCISION

RELATED APPLICATIONS

This is a divisional of U.S. application Ser. No. 08/195,337, filed on Feb. 14, 1994 now U.S. Pat. No. 5,514,153. Application Ser. No. 08/195,337 is a continuation-in-part of U.S. application Ser. No. 07/792,730, filed on Nov. 15, 1991 now U.S. Pat. No. 5,295,994, and a continuation-in-part of U.S. application Ser. No. 08/054,416, filed on Apr. 28, 1993 now abandoned. Application Ser. No. 08/054,416, in turn, is a divisional of U.S. application Ser. No. 07/487,645, filed on Mar. 2, 1990 now U.S. Pat. No. 5,331,975. The benefit of the earlier filing dates of the aforementioned applications is hereby claimed.

BACKGROUND OF THE INVENTION

The present invention relates to medical devices, and particularly to expandable medical devices such as cannulas, catheters, retractors, and similar devices.

Existing cannulas and/or retractors as used in endoscopic surgery today are passive devices which are fixed in length and width. They can not be varied intraoperatively in length and width to accommodate larger devices or varying size devices through the skin.

Skin and subcutaneous (subsurface) tissues are viscoelastic: they will gradually stretch without tearing. Once the tissue is slowly stretched it maintains its expanded condition for a period of time. Alternatively, the tissue can be stretched further, for example to progressively stretch out an incision. Then, after relaxation, the tissue will regain its original unstretched condition without having been damaged.

Current methods used for retracting tissue and improving visualization are mechanical separation using metal retractors during open surgery, or the direct pressure of an unconfined flow of fluid such as water or $CO_2$ during fiberoptic surgery. A typical mechanical external fixator has pins driven through the bones and mechanically distracts the elements of the joint. Problems with the water method include fluid extravasation including into and through the tissue itself. Increased pressure and swelling result in the area, resulting in edematous or swollen tissue. Excess pressure from mechanical retractors may cause necrosis or tissue death. With these methods, it is impossible to monitor the pressure being applied to the body tissues, and tissue damage or necrosis can result.

While operating from within the body, i.e., fiber optic assisted surgery as opposed to open surgery, there is no known way to selectively move or retract tissue, either hard tissue such as bone or soft tissue, out of the way to improve visualization. No device in use adequately allows a surgeon to create an actual space or expand a potential space in the body, by separating adjacent layers of tissue. The prior art does not disclose a retractor which is powerful enough and made of a material which is strong and resilient enough to, for example, separate tissue planes from within. Such a device, especially in the field of fiber optic surgery, would allow a surgeon to visualize and operate without using the conventional bulky and awkward mechanical retractors which require large open incisions. Such a device would also permit working within the body without damaging a great deal of tissue in the path between the skin opening and the working area, by minimizing the external orifice or skin incision.

SUMMARY OF THE INVENTION

The present invention is a system of retractors and/or cannulas with which a surgeon can use to take potential spaces within the body and turn them into existing spaces safely and easily and controllably in order to safely visualize appropriate tissue and operate. The cannula and/or retractor selectively moves appropriate tissue out of the way to enable a surgeon to see and work better within the body, and selectively moves body parts such as joint parts or soft tissue planes in order to create a space between the tissues for visualization and for working.

A cannula and/or retractor of the present invention may have a fluid-operated portion such as a balloon or bladder to retract tissue, not merely to work in or dilate an existing opening as for example an angioscope does. The fluid-filled portion is flexible, and thus there are no sharp edges which might injure tissue being moved by the retractor. The soft material of the fluid-filled portion, to an extent desired, conforms to the tissue confines, and the exact pressure can be monitored so as not to damage tissue. The expanding portion is less bulky and more compact, and the pressure it applies at the tissue edges can stop bleeding of cut tissue. These are all features not possessed by a conventional mechanical retractor.

With a typical mechanical retractor, the opening in the skin and thence inwardly must be larger than the surgical area being worked upon, in order to be able to get the mechanical retractor into position. The surgeon must damage a large amount of tissue which may be healthy, in order to expose the tissue to be worked on. The cannula and/or retractor of the present invention minimizes damage to tissue in the way of the tissue the surgeon needs to expose, which was previously cut in a large open exposure. With the cannula and/or retractor of the present invention, the opening at the skin is smaller at the skin where the device is inserted, and wider at the location inside the body where the cannula and/or retractor is expanded. The cannula and/or retractor is first placed into the body in an unexpanded condition, and then, as it is expanded, pushes tissue out of the way in deeper layers of the body one can see and safely operate on affected tissue. Thus, less undesired tissue damage occurs.

The bladder is pressurized with air or with water or another fluid. The fluid used in the bladder must be safe if it accidentally escapes into the body. Thus, besides air, such other fluids as dextrose water, normal saline, $CO_{21}$ and $N_2$ are safe. The pressure in the bladder is monitored and regulated to keep the force exerted by the retractor at a safe level for tissue to prevent tissue necrosis. The retractor can exert a pressure on the tissues of as high as the mean diastolic pressure of 100 mm of mercury, or higher for shorter periods of time, while still being safely controlled. Typical inflatable devices such as angioscopes do not have anywhere near the strength, or the ability to hold enough fluid pressure, or shapes to retract tissue as described herein. As compared to prior art devices, the retractor of the present invention operates with greater pressure within the bladder, since it is made of stronger materials such as Kevlar or Mylar which may be reinforced with stainless steel, nylon, or other fiber to prevent puncturing and to provide structural shape and support as desired. Such materials are strong enough to hold the necessary fluid pressure of about several pounds or up to about 500 mg Hg or more and exert the needed force on the tissue to be moved. The choice of material is well within the ability of one familiar with such materials and accordingly will not be gone into in further detail herein. The present retractor is thus able to exert substantially more force on adjoining tissues than a prior art device. The shapes of the retractors are specific for each application, and may include separate variable chambers which are sequentially controllable, to control the direction of tissue retraction.

Surgeons operate along tissue planes. Once a surgeon finds a tissue plane, he dissects along it, starting the separation process with the knife. The cannula and/or retractor holds the tissue layers apart and helps and eases in defining and further separating the tissue layers as the surgeon operates along the tissue planes, helping to spread and define the planes. The cannula and/or retractor helps to separate the tissue layers, increasing the space for operating, and improving the surgeon's ability to separate and visualize, leading to better and safer surgical technique.

A preferred use for the present retractor is in the field of fiber optic surgery, including endoscopy, arthroscopy, laparoscopy, etc. which require looking into and operating within a limited space with a fiber optic light and camera. The bladder expands into an area of soft tissue—for example the bursa—and pushes it out of the way. The bladder can be left in place during the operation, or it can be deflated and removed, and the arthroscope and other instruments can be put into the space created.

The bladder may be a bellows type device in which the material does not stretch but which expands when pressurized from within and which is collapsed by the use of suction. In this case, it would preferably be made of a polymer of the class including Kevlar or Mylar fabric for strength and structural integrity. The bladder may generally also be made from any very thin walled polymer.

The bladder may also be made from a biocompatible and/or biodegradable material, so that if it can not be removed from the body for some reason, or if the surgeon desires to keep the bladder in place in the body for a period of time, it will not damage the tissue and may eventually be reabsorbed into the body. Such a biodegradable bladder may be left under the skin postoperatively to stop postoperative bleeding or to keep tissue expanded. Alternatively, the bladder may be made of a stretchable material which stretches when pressurized from within, and then collapses partially of its own accord when depressurized or also with the help of suction. The retractor may be transparent for better visibility, but it need not be for some applications. Also, the retractor can be disposable. The material choice is within the skill of the art. One surface of the bladder may be made of or have thereon a reflective surface to reflect light to see around a corner.

A most typical construction for the cannula and/or retractor of the present invention is an inflatable bladder situated on the end of a shaft, which may be flexible or rigid, which is pushed through an extra opening in a scope or cannula or through a separate portal, and which expands at the end of the shaft.

The retractor can be located on a scope, either on the end thereof or movable axially through a channel along the length of the scope. The retractor can alternatively be mounted on a cannula. The retractor can be mounted on a separate shaft passing through an existing channel in a cannula; it can be inserted through a separate hole in the cannula or the scope; or it can be inserted through a separate opening in the body. The shaft with a retractor on the end can be pushed or slid through the cannula, side by side with a scope. Alternatively, the bladder can expand out of, then recess back into, a groove on a cannula or scope. The retractor can be used to create a space right by the scope, or possibly at a location spaced from the end of the scope.

The bladder itself can be round, eccentric, oval, conical, wedge-shaped, U-shaped, curved, angled, or it may be in any shape desirable to optimize the particular application. The bladder may be irregularly shaped when inflated, that is, it may expand to a greater radius in the area where it is desired to look (where greater exposure space is needed).

Vacuum can be used to deflate the bladder. The bladder may then be removed by sliding it out the portal directly.

The present invention is described herein as relating to cannulas and/or retractors. A cannula is a device for insertion into or through body tissue to provide a working passage for surgical instruments, scopes, etc., as in endoscopic or arthroscopic surgery. A catheter, on the other hand, is an artificial fluid passage primarily used for insertion through an existing body opening. The two types of devices have very different structures and structural requirements. For example, a catheter is usually flexible, very small in diameter, and not suitable for maintaining a working passage through normally closed body tissues, while a cannula is more rigid, larger in size, and designed specifically to provide a working passage for surgical instruments and scopes through normally closed body tissues. It should be understood, however, that many of the features of the present invention can with suitable modifications be applied to the catheter art. Accordingly, the present invention is not limited to cannulas per se, but may be applicable to catheters or other devices also.

The present invention defines an active cannula or sleeve which does more than merely maintain a channel or passage. It is an active device usable to enlarge a channel or passage, to position a scope or instrument, to move or locate tissue, etc. The cannula can vary in size or shape as needed, intraoperatively. Typically, with a passive (non-expandable) cannula, a surgeon must make an incision in the skin and muscle large enough to receive the largest instrument to be passed through the incision to the surgical area. Because a cannula of the present invention is expandable, the surgeon can make a small relatively small incision, stretch the tissue with the expandable cannula, contract the cannula and remove it, allowing the skin to come back to its unstretched condition. Thus, a smaller incision can be made to fit the same size instrument. This results in less trauma and scarring and an easier operation.

Further, known cannulas are generally round, while skin expands (from an incision) in an elliptical fashion, between tissue planes. Thus, the present invention provides cannulas which are or can assume such a noncircular shape, to fit into the natural opening and cause less trauma.

The devices of the present invention are usable in endoscopic procedures generally. The devices can be used to seal off a space; to expand an existing space or a potential space for working or visualization; to move tissue (for example, to stretch an incision) or to protect it. Other uses within the skill of the art but not enumerated herein are within the scope of the invention.

The cannulas of the present invention allow for the progressive stretching of an incision in skin or subsurface tissue in order to allow improved exposure, while minimizing damage to the tissue by making the actual incision as small as possible.

In the arthroscopic model, a fixed cannula is placed through the skin to the subsurface tissues into a joint. Different size working devices (shavers, burrs, scissors, punches, scope, etc.) are placed through the cannula to visualize or to work in the subsurface area at the distal end of the cannula. The cannula can be progressively expanded or stretched radially outwardly, to stretch or expand the skin and subsurface tissues. The cannula typically expands along its entire length, although it may in some cases be expandable at selected portions along its length.

The expansion can be in a circular pattern, or it can be in an oval or elliptical or other pattern to accommodate (a) the tissue planes or (b) the instruments being inserted through the cannula.

The cannula can expand inwardly to act like a valve or a seal. Or it can expand both inward and outward.

The cannula is preferably flexible—that is, it is bendable about an axis extending perpendicular to the longitudinal extent of the cannula. In other words, the cannula as a long straight object is not rigid but can bend so that it is not straight. This allows the cannula to conform to the body tissues to the extent desired.

All cannula bodies can be multi-lumen for passages through which extend structure for control of bladders, tools, scope, etc.

In a first embodiment, a cannula may be of a stretchable material (such as a polymer) which is introduced into the body with a trocar. The trocar is then removed. Progressively larger dilating devices are placed inside the stretchable cannula, as needed, to progressively stretch out the skin and tissue to a larger size in order to introduce larger instruments through the cannula. Each time the cannula is enlarged, the stretched tissue remains in its stretched condition for a period of time because of its viscoelastic properties.

One way of stretching the cannula is by placing inside the stretchable cannula a bladder (round or elongated in the shape of a sausage, for example) which can be inflated to uniformly stretch the cannula and tissue. The bladder can be deflated and removed, leaving the enlarged opening.

In a second embodiment, the cannula is itself inflatable for expansion. The cannula is basically an inflatable cylinder with expansions in both the inner diameter and the outer diameter. As inflated, the device expands to a preformed shape with the inner diameter following the outer diameter and expanding outward to create a progressively larger opening. Filaments or cords can be placed between the inner and outer walls to limit their separation from each other. The inner wall can be more rigid.

In a third embodiment, the cannula includes one or more stretchable (inflatable or expandable) parts and one or more non-stretchable parts. The non-stretchable parts can be metal or plastic pieces such as curved plates, joined by the stretchable elements which extend longitudinally between them. These stretchable elements can be bladders. As larger devices are passed through the cannula, the stretchable portions expand and the plates move outwardly to stretch an appropriate opening.

In any of these cases, one can monitor and control the amount of pressure being applied to the tissue upon expansion of the cannula, so as to not exceed a certain critical pressure and damage tissue. This can be done by monitoring the actual size of expansion, the amount of air or fluid introduced to inflate the device, the fluid pressure within the device, etc.

There are numerous possibilities of a cannula-with-bladder or (catheter-with-bladder) construct.

One specific example is an arthritis irrigation system. This is a multi-lumen tube which has one lumen/portal for inflow of irrigation fluid and a second portal for suction (return). The tube is flexible and has its distal end placed in a joint to be irrigated. The tube is fixed in place by an expanding device as discussed There can be one or more bladders at any given location or on any given instrument. Multiple bladders can be controlled as independent structures or as one unit. Specific structure and control is based on the particular application.

The surface of the material can be pebbled or roughened or ridged, or have serrated edges, to better grip tissue and hold the retractor in position. Of course, the surface must still remain smooth enough so that the retractor is easily removable without damage to the tissue it contacts.

The bladders can expand by well in excess of 200%.

The bladder is preferably made of an elastomeric material which is strong enough to move tissue as desired. A suitable material for the expandable bladder is Silastic® elastomer, which is available from Dow Corning in medical grades. Other suitable materials are silicone, or latex, or PVC.

The bladder may be made of a non-elastomeric material which is strong enough to move tissue as desired. A suitable material is Mylar® fabric. A non-elastomeric material may have a more controllable shape because it will not stretch. A non-elastomeric material will collapse inward automatically due to the pressure of the tissue around it, whenever it is not inflated. Many of the illustrated embodiments which are discussed as being made below. Fluid flowing through the joint flushes out debris in the joint. The device can include third or additional lumens for a scope or tools to pass through. Since the tube is both flexible and fixed in place, it can remain in the patient even when the patient is ambulatory. It thus provides a permanent passage for the surgeon to access the joint.

There can be multiple bladders at a location on the cannula, independently controlled, to position the cannula. At least one bladder is preferably at the tip of the device to expand or stretch tissue or to stabilize the device.

In any of the illustrated embodiments, the bladder can be made of a different material from the cannula, as opposed to, for example, a Fogarty catheter which is made of all one material. This will allow for variations in construction, with the bladder being made of one material to better perform its functions and the cannula or other supporting member being made of another material to better perform its functions.

The expanding (inflatable) bladders of the present invention are constructed in various manners as set forth below. The bladder can stretch cannula walls. The bladder can move tissue and allow selective manipulation of tissue, even arthroscopically. The bladder also has a tamponade effect, lessening bleeding in the surrounding tissues.

The bladder also distributes the retractive force, reducing stress on delicate tissues such as nerve tissue. of an elastomeric material can also be made of a none-lastomeric material.

The expandable bladder can be made of a biodegradable material. In such a case, the biodegradable portion can be made detachable from the remainder of the retractor, so that it can be detached and left in the body after surgery. This is useful, for example, to prevent adjacent tissue planes from scarring together after surgery. The biodegradable mass will in time disappear, allowing the tissues to adjoin after they are healed.

The bladder can be made of a composite material—that is, a particle or fiber-reinforced material. Many suitable materials are in use in industry. Composite materials can be made stronger while still retaining flexibility and fluid-sealing capabilities. Composite materials also provide the capability to have a bladder assume a specific shape upon expansion.

The bladder can be made of a composite biodegradable material.

The bladder(s) can be made of two different materials bonded together, such as a stretchable (low-modulus) and a non-stretchable (high-modulus) material. Mylar® and Silastic® are suitable materials, or metal for a stiff material. As the inflation fluid (typically air) is introduced, it takes the path of least resistance and the non-stretchable material fills out to its expanded shape first. Then the stretchable material expands, in a manner constrained by the already-expanded non-stretchable material.

The bladder can be made of a transparent material to provide a better view of the operating area and improved visualization.

The bladder may have a dual durometer layered construction, with a thin layer for fluid retention overlying a thicker layer for shaping. Other laminated constructions are possible, also.

The external shape of the retractor when expanded, and the amount of expansion, are designed for the specific application on which that retractor is to be used. For example, if the surgeon is working against bone, he can select a retractor which is configured so that it stays flat against the bone, and expands away in the opposite direction, to push tissue away from the bone and create a working and visualization space next to the surface of the bone.

There are several ways to control shape of expansion- thick and thin areas (gaps, ridges, stiffened areas, etc.), fiber reinforcing, dual durometer construction, different materials affixed together, tethering cords, and pre-shaping.

Upon application of a given amount of force, a thinner material will stretch more than a thicker material. Thus, all other factors being equal, an inflatable device will stretch more where it is thinner, and will stretch less where it is thicker. This occurrence can be used to control the shape into which a bladder expands when it is inflated by fluid under pressure.

As a simple example, it can readily be seen that if a bladder has one half made of a very thick material and one half made of the same material but much thinner, then upon the introduction of fluid under pressure, the thin material will stretch more quickly (easily), and the bladder will expand unevenly. The thin half of the bladder will deform more under the same pressure until the force needed to stretch it further is equal to the force needed to stretch the thicker material. The half made of the thicker material will then begin to stretch, also. Thus, the thickest point on the wall will be at the crown area (farthest out).

The areas of variation in cross section can be of various shapes and directions to control the expansion rates. For example, the circumference of a bladder can be configured as an incomplete hoop. Thus, most of the circumference is of a thicker material, while selected areas are thinner. Upon the introduction of fluid under pressure, the thinner areas will expand first, with each thicker area moving outwardly as a whole.

There can be ribs around the circumference. Areas of thickness or thinness can extend longitudinally, circumferentially, radially, or in broken segments.

A second way to control the shape of expansion is the use of a fiber reinforced (composite) material. The direction of the fibers, along with their number, spacing, layering, and length, controls the rate of expansion of the matrix material. Also, areas devoid of fibers will expand faster or further than areas with more or stiffer fibers.

Specifically, the fibers resist stretching along their length. Thus, the bladder will stretch more in a direction across the fibers, or where the fibers are not present, than in a direction along the fibers. Fibers can be placed at the edge of the bladder to maintain the shape of the bladder when inflated. Fibers can be layered, with one layer in one direction and another layer in another direction to control expansion in the other direction. Fibers can be placed in overlapping layers, to allow expansion in one plane only.

Adding fibers makes the bladder more puncture and tear resistant. Note that the bladder can, for this purpose, also be made of or include a self-sealing material.

A third way of controlling expansion shape is to pre-shape the bladder to assume a certain form when expanded. This is done in the molding process. The bladder is typically formed on a mandrel which is of a particular shape and which is sized about half way between the unexpanded and the expanded size of the bladder.

The pre-determined shape of the unexpanded bladder is basically a combination of varying wall thickness and ribbing, made on a three part mold.

In certain experimental models constructed to date, the bladder is bonded onto a nylon stalk of 7 mm O.D. The bladder is stretched from about 3 mm to about 7 mm at its smallest dimension. This pre-stretched area puts the material under tension. Any larger diameter portions are relaxed. As the bladder is expanded, the smaller diameter portion, which is already partially expanded, stretches at a limited rate. The larger diameter portion (under no load) expands at a faster rate. They balance out at a point where all the material is under basically the same load in tension. This is the point at which the shape is attained.

It should be understood that this particular example and its dimensions are not limiting, and that any diameter can be used. This is an example of a specific sized cannula for a specific application.

With a typical material (silicone), the more you stretch the material, the more force is needed to stretch it further.

The prestretching of the bladder is done so that the bladder lies flat on the cannula body. The bonding areas are such that as the expansion takes place the material expands radially outwardly as well as axially.

It can alternately be doubled up at a certain area, such as the tip of a stalk or cannula. This will allow maximum expansion at the tip.

Tethering cords can be fixed to bladder portions and extend between them to control and/or limit the expansion of the bladder. This can be done with bladders made of a composite material or including plates or other thicker areas. In a cannula construct, the tethering cords can run between the cannula body to the crown of the bladder to control and/or limit its expansion.

Plates can be added in which will limit the shape of the bladder or create an edge. For example, if a flat plate is added, the bladder can expand in a circular fashion but the flat plate will remain flat and provide a flat area on the outside of the bladder. Or the plate can be circular, or at an angle to create an edge. There can be multiple such plates added to create specific shapes. Tethering cords can be used to extend to the plate. This can be useful in the cannula construct.

The bladder can also have a bellows-type construction for increased expansion control and structural rigidity.

Suction can be used to collapse any of the devices to facilitate removal.

BRIEF DESCRIPTION OF THE DRAWINGS

The foregoing and other features of the present invention will become apparent to one skilled in the art upon a consideration of the following description of the invention with reference to the accompanying drawings, wherein:

FIG. 1 is a side elevational view of a joint irrigation apparatus;

FIG. 2 is a longitudinal sectional view through the apparatus of FIG. 1;

FIG. 3 is a view taken along line 3—3 of FIG. 1;

FIG. 4 is a view of an alternate embodiment of the apparatus of FIG. 1;

FIG. 5 is a transverse sectional view through an expanding cannula;

FIG. 6 is a view of the cannula of FIG. 5 in an expanded condition;

FIGS. 7A and 7B illustrates a cannula having an outwardly expanding bladder formed within the wall of the cannula;

FIGS. 8A and 8B illustrates a cannula having an inwardly expandable bladder formed in the wall of the cannula;

FIGS. 9A and 9B illustrates a cannula having an inwardly and outwardly expanding bladder formed within the wall of the cannula;

FIG. 21 is a schematic view of a retractor shown mounted on the end of a cannula and having an opening therein for a scope to pass through;

FIGS. 38–43 illustrate longitudinally extending radially expansible cannula segments;

FIGS. 46–49 illustrate a cannula having an expandable bladder portion with a varying wall thickness;

FIGS. 50–52 illustrate flexible bladder portions having relatively rigid members molded therein;

FIGS. 53 and 54 illustrate rigid members molded into the elastomeric material of an inflatable bladder circumscribing a cannula or other medical device;

FIG. 57 is a schematic illustration of a cannula having the same general construction as the cannula of FIGS. 55 and 56, the cannula of FIG. 57 having tethers and being shown in a retracted condition;

FIG. 58 is a schematic illustration of the cannula of FIG. 57 in an extended condition with the tethers restraining movement of a flexible wall portion of the cannula;

FIG. 59 is a schematic illustration of a cannula having the same general construction as the cannula of FIG. 58, the cannula of FIG. 59 having a plurality of tethers disposed within a chamber formed by the expanded flexible wall of the cannula;

FIG. 60 is an end view, taken generally along the line 60—60 of FIG. 59, illustrating the manner in which a plurality of tethers are connected with the flexible wall of the cannula;

FIG. 61 is a sectional view, taken generally along the line 61—61 of FIG. 59, illustrating the manner in which a plurality of tethers extend outwardly from a main section of the cannula toward an inner side surface of the flexible wall of the cannula;

FIG. 62 is a sectional view, taken generally along the line 62—62 of FIG. 59, illustrating the manner in which a plurality of tethers extend outwardly from a main section of the cannula towards the inner side surface of the flexible wall;

FIGS. 68–76 illustrate a variety of bladder devices including reinforcing fibers and/or tethering cords.

DESCRIPTION OF PREFERRED EMBODIMENTS

Figures 10A, 10B, 10C:
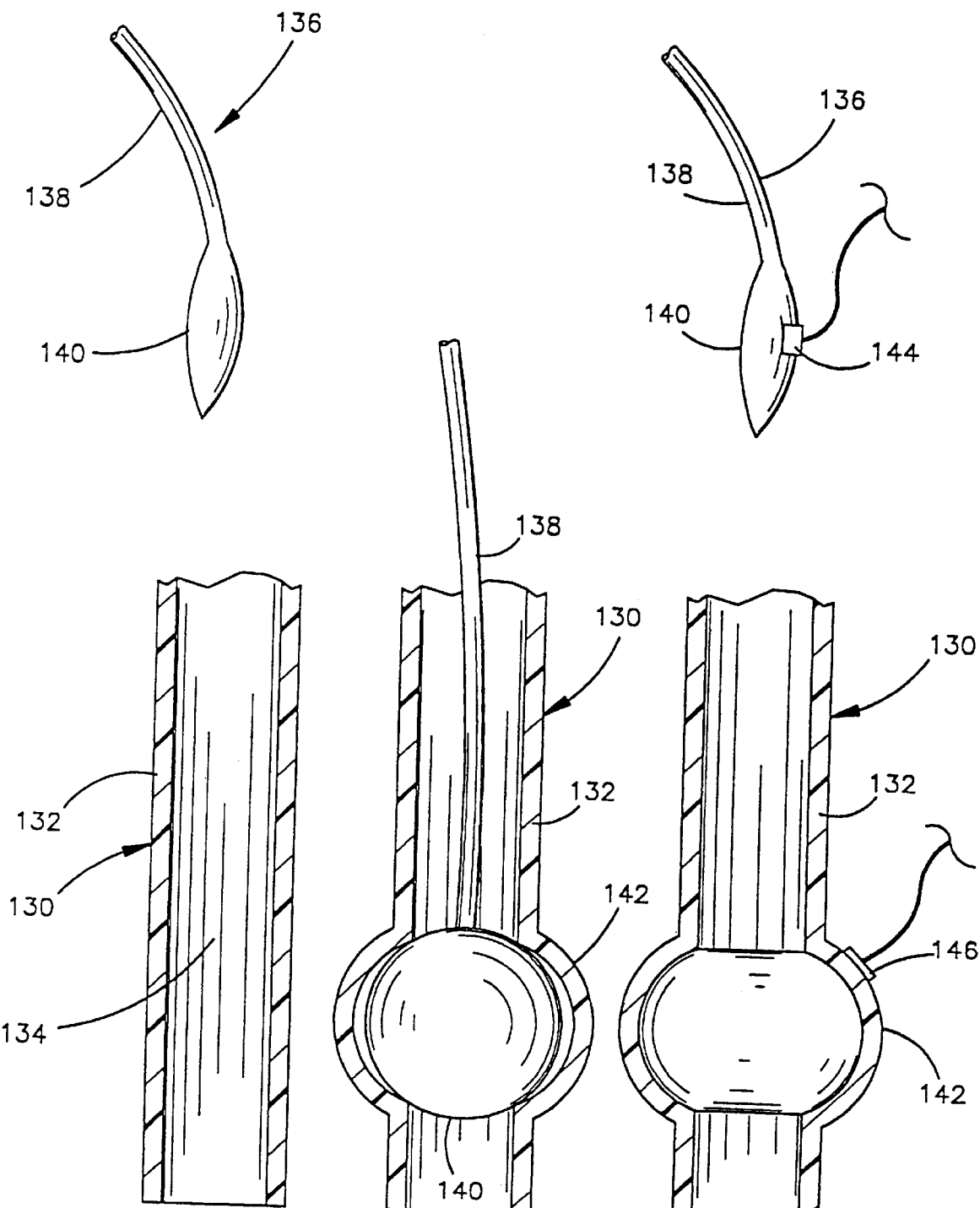
FIGS. 10A–10C illustrate the expansion of a cannula having viscoelastic walls by means of an inserted inflatable member.

FIGS. 1–3 illustrate an arthritis irrigation apparatus 10. The irrigation system 10 includes a cannula 12 having a disc portion 14 and a longitudinally extending cannula body 16. A central wall 18 divides the cannula body 16 into two longitudinally extending lumens 20 and 22.

An expandable bladder 30 is connected to or formed integrally with the cannula 12 at the distal end 32 and proximal end 34 of the cannula body 16. The expandable bladder 30 includes a longitudinally extending wall portion 36 and a transversely extending wall portion 38. The expandable bladder 30 is supplied with fluid under pressure through a fluid supply port 40 closed by a rubber diaphragm seal 42. The lumens 20 and 22 are closed by similar diaphragm seals 44 and 46, respectively. The cannula body 16 has a recessed portion 48 in which the bladder 36 fits when unexpanded.

The system 10 is inserted into a pre-made opening until the disc portion 14 engages the skin. Upon the introduction of fluid under pressure into the expandable bladder 30, the bladder 30 expands from the unexpanded condition illustrated in FIG. 1 to the expanded condition illustrated in FIG. 2. The bladder wall 36 moves radially outwardly, and skin or other tissue is trapped between the bladder wall 38 and the distal surface 49 of the disc portion 14 of the cannula 12.

The system 10 is thus locked in place, with the distal end 32 in position in a joint. Appropriate instruments may then be inserted through the diaphragm seals 44 and 46 into the lumens 20 and 22, respectively. For example, flushing fluid may be supplied to the joint through the lumen 20, while it is removed from the joint by suction through the lumen 22. When the joint is not being flushed, the diaphragm seals 42, 44 and 46 seal the openings in the system 10, and the expanded bladder 30 retains the system 10 in place in the body.

It should be understood that any number of lumens, other than two, can be included in the cannula body 16. The number of lumens is limited only by the size of the instruments to be inserted through the cannula body 16. In a preferred embodiment, the disc portion 14 of the cannula body 12 is about the size of a nickel, with the cannula body 16 being correspondingly smaller. Of course, the dimensions and arrangement of the various portions of the system 10 could be modified to enable the placement of other instruments through the cannula body 16.

Each of the lumens may have a controllable inflow-outflow portal. These can be substituted for the diaphragm seals. These portals may be a simple tube with an on-off valve attached, as is known in the art, or can be another suitable structure.

FIG. 4 illustrates an alternate embodiment of the system 10 in which a system 50 includes a round or doughnut-shaped bladder 52 extending between the distal end 32 and the proximal end 34 of the cannula wall 16. This doughnut-shaped bladder can be easier or less expensive to manufacture, and also can provide more cushioning effect to the tissues which it engages. Again, tissue is trapped between the bladder 52 and the disc portion 14 of the cannula 12, to retain the system 50 in place in the body.

FIGS. 5 and 6 illustrate a variable size cannula in which inflatable bladders push apart two relatively rigid portions to move tissue. FIGS. 5 and 6 are transverse cross sections through a longitudinally extending cannula 60, which can be any desired length. The cannula 60 expands radially outwardly along its length.

The cannula 60 includes a first C-shaped portion 62 having ends 64 and 66 and a second C-shaped portion 68 having ends 70 and 72. An inflatable bladder 74 has one end portion 76 fixed to the end portion 64 of the portion 62. The opposite end portion 78 of the bladder 74 is fixed to the end portion 70 of the portion 68. Similarly, a bladder 80 has one end portion 82 fixed to the end portion 66 of the portion 62, and its second end portion 84 fixed to the end portion 72 of the portion 68.

The portion 62 has an outwardly facing surface 86 and the portion 68 has an outwardly facing surface 88. The cannula 60 has a central opening 90 which is enlarged in size upon expansion of the bladders 74 and 80 to provide a larger working space while reducing tissue damage. Upon the introduction of fluid under pressure into the bladders 74 and 80, the portions 62 and 68 are moved away from each other to engage tissue with their surfaces 86 and 88, respectively. The relatively rigid portions 62 and 68 provide increased pushing strength of the cannula 60 as compared to a soft inflatable bladder. Further, the cannula 60 also holds its structural shape better and is able to maintain the opening better. Thus, with the cannula 60, a limited incision can be made in the tissue, which incision is then enlarged by the cannula itself rather than with a cutting device. The application of suction to the bladders 74 and 80 causes them to deflate to return the cannula 60 to its unexpanded condition. The tissue is viscoelastic and thus will stretch out during its expansion by the expander 60, and then return to its original unexpanded shape, i.e., the original size of the incision after removal of the cannula. Thus, less tissue damage results.

Cannulas in accordance with the present invention may have one or more bladders as part of the cannula wall. These may create inward or outward expansion. For example, FIGS. 7A and 7B illustrate a longitudinal portion of a cannula 92 having a wall portion 94 defining a central opening 96 through which surgical instruments or the like can be passed. The wall portion 94 includes a portion 98 partially defining a fluid chamber 100 which may be supplied with fluid under pressure through a fluid supply line 102 extending through the cannula wall 94. On the introduction of fluid under pressure into the volume 140, the wall portion 98 of the cannula 92 expands radially outwardly, from the unexpanded condition of FIG. 7B to the expanded condition of FIG. 7A, as a seal or retainer against tissue.

Similarly, the cannula 104 illustrated in FIGS. 8A and 8B includes a wall 106 having an inner portion 108 defining a fluid volume 110. Upon the introduction of fluid under pressure through a supply passage 112 in the wall 106, the wall portion 108 expands radially inwardly to close at least partially the central opening 113 in the cannula 104. The expanding portion 114 of the cannula 104 thus acts as a valve or seal for the central opening 110 of the cannula. This can be very useful if it is desired to close the central opening 110 while leaving the cannula 104 in place in the body tissue. The central passage 113 can also be closed completely. Alternatively, the wall portion 108 can lamp onto an instrument or scope extending through the passage 113 to lock it in place.

In addition to the cannula inner seals or valves formed by the radially inwardly expanding bladder walls, the present invention contemplates cannula inner seals formed by other structures. For example, a simple mechanical seal can be used such as a diaphragm seal like the seals 44 and 46 (FIGS. 1–3). Other forms of mechanical seals can be used, such as a membrane (iris) valve, screw lock, twist lock, or luer lock. It is intended that these alternatives be included within the scope of the invention.

FIGS. 9A and 9B illustrate a cannula 116 having an expanding portion 118 in its wall 120. Upon the introduction of fluid under pressure through a fluid supply passage 122 in the wall 120, a portion 124 of the cannula wall 120 expands radially outwardly while a longitudinally co-extensive portion 126 of the wall 120 expands radially inwardly to partially or completely close a central longitudinally extending passage 128. Thus, the cannula 116 has a portion 118 which expands both inwardly and outwardly. The cannulas of FIGS. 7–9 thus illustrate the principle of expanding either inward or outward or both at selected axial locations along the longitudinal extent of a cannula.

FIGS. 10A–10C illustrate the expansion of a stretchable cannula by an expandable member inserted therein. A cannula 130 has a wall 132 defining a central longitudinally extending passage 134. The cannula 130 is made of a stretchable material having viscoelastic properties whereby the wall 130 when stretched outwardly will retain its stretched condition for a period of time. An expander 136 includes a stalk 138 on the end of which is mounted an expanding portion 140. Upon insertion of the expander 136 into the cannula 130 as illustrated in FIG. 10B, the expanding portion 140 may be expanded radially outwardly by the introduction of fluid under pressure through the stalk 138, to stretch a wall portion 142 of the cannula wall 132 radially outwardly. Upon subsequent deflation of the expanding portion 140 of the expander 136, and removal of the expander 136 from the cannula 130, the cannula wall portion 142 remains in its stretched condition for at least a period of time. The cannula 130 is thereby retained in place in the surrounding tissues while instruments or a scope can be passed through it.

The present invention contemplates monitoring the pressure applied to tissue by the expanding cannula. This can be done, for example, with any known pressure sensor or strain gauge. Such is indicated schematically at 144 in FIG. 10C as being on the wall of the device 136 used to stretch the cannula 130. Alternatively, it is indicated schematically at 146 in FIG. 10C as being on the wall of the cannula 130.

Figure 11:
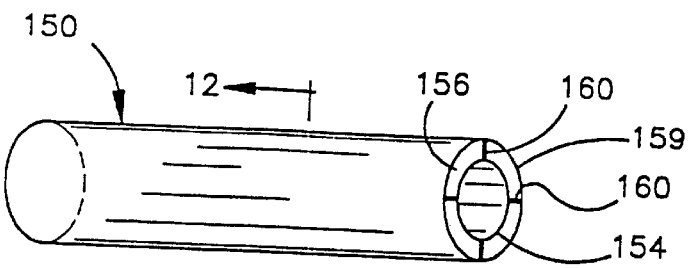
FIGS. 11–13 illustrate a cannula comprising a cylinder expandable along its entire length.
Figure 12:
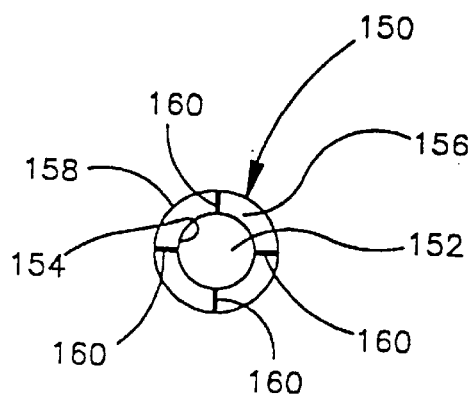
Figure 13:
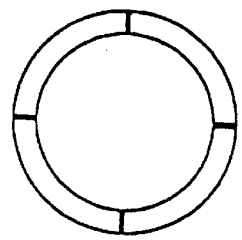

FIGS. 11–13 illustrate a cannula 150 which comprises a cylinder expandable along its entire length. The cannula 150 has a central longitudinally extending working passage 152 defined by an inner wall 154. An inflation space 156 separates the inner wall 154 from an outer wall 158 of the cannula 150. A series of tethering cords 160 extend between the inner wall 154 and the outer wall 158.

The inner and outer walls 154 and 158, respectively, of the cannula 150 are constructed so that, upon the introduction of fluid under pressure into the inflation space 156, both walls expand radially outwardly to a larger diameter. Fluid is introduced through a fluid inflow means (not shown) which may be a simple tube or valve in fluid communication with the inflation space 156. The cannula 150 expands from the condition shown in FIG. 12 to a further expanded condition as illustrated in FIG. 13. The tethering cords 160 limit movement of the outer wall 158 of the cannula 150 from the inner wall 154 of the cannula 150. In a preferred embodiment, the tethering cords 160 comprise fibers (either solid or stranded) having their ends fixed to the inner wall 154 and the outer wall 158 and extending therebetween. The tethering cords 160 may be unextensible, or they may be somewhat extensible upon the application of a relatively large amount of force. Use of the tethering cords 160 is advantageous in that it allows for controlled expansion of spaced portions of an inflatable device.

Figure 14:
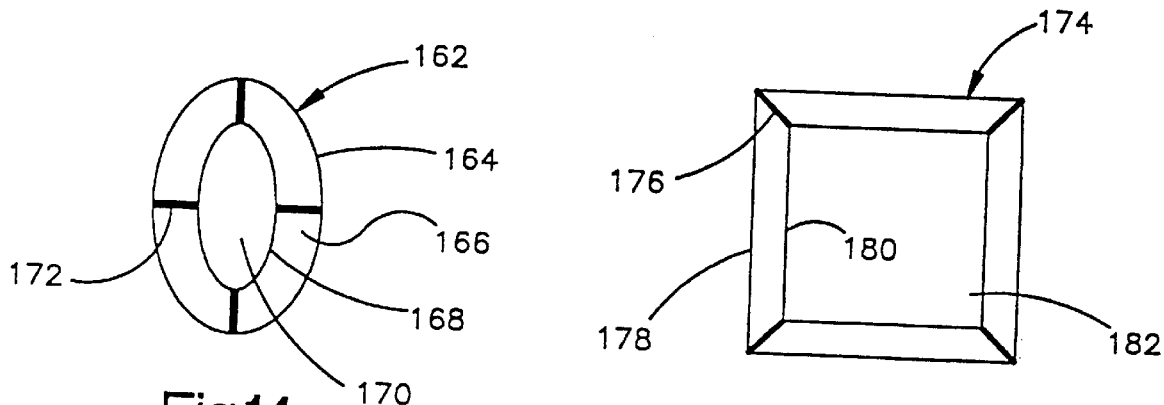
FIG. 14 illustrates an elliptical or an oval-shaped cannula having tethering cords.

The cannula 150 is circular in cross sectional shape. It should be understood that the present invention is not limited to circular cannulas, but specifically contemplates the provision of cannulas of any type described herein of other cross sectional shapes. The cross sectional shape of a particular cannula may be selected in accordance with a particular application for that cannula. For example, an elliptical or oval-shaped cannula 162 (FIG. 14) may be more suitable for insertion between adjacent tissue planes, as it conforms more to the opening between the tissue points. The oval-shaped cannula 162 includes an outer wall 164, an inflation space 166, an inner wall 168, and a working passage 170 extending axially therethrough. Optionally a plurality of tethering cords 172 extend between the inner wall 168 and the outer wall 164, and limit movement of the outer wall 164 from the inner wall 168.

Figure 15:
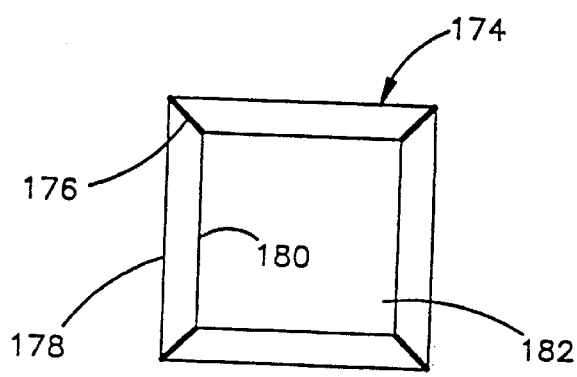
FIG. 15 illustrates a square-shaped cannula having tethering cords.

FIG. 15 illustrates, as exemplary of the other shapes of cannulas which may be provided, a rectangular (in this case square) shaped cannula 174 optionally having a plurality of tethering cords 176 extending between the outer cannula wall 178 and an inner cannula wall 180. The inner wall 180 defines a working passage 182 extending longitudinally through the cannula 174.

Figure 16:
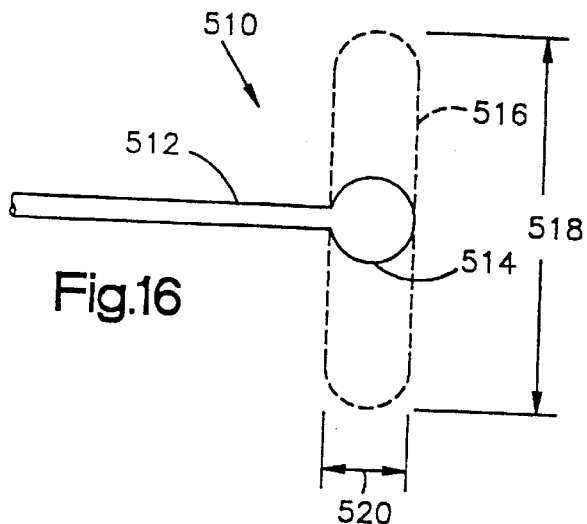
FIG. 16 is a schematic view of a retractor shown in the unexpanded or contracted and expanded or extended conditions.

FIG. 16 illustrates schematically a retractor 510 in accordance with the present invention. The retractor 510 includes a fluid supply structure 512 and an expandable balloon or bladder 514 having a flexible wall located at or near the end of the structure 512. The bladder is expandable, under the force of fluid under pressure, from an unexpanded or retracted condition as indicated in full lines at 514 to an expanded or extended condition as shown in broken lines at 516. In the expanded condition, the transverse dimension 518 of the bladder 514 is significantly greater than its transverse dimension before expansion, that is, the dimension 520. Also, in the expanded condition, the transverse dimension 518 of the bladder 514 is significantly greater than its longitudinal dimension 520.

Figure 17:
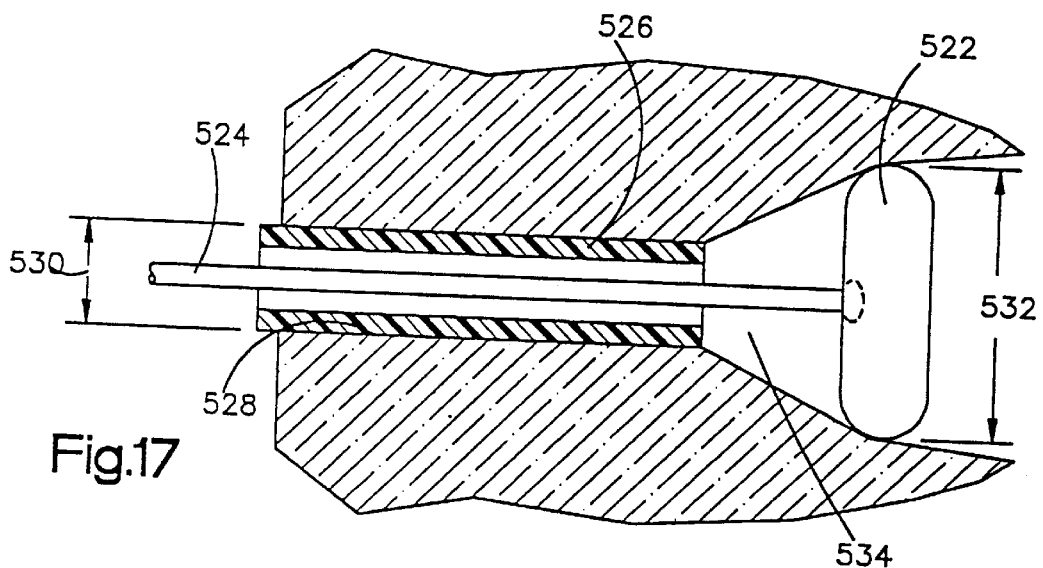
FIG. 17 is a schematic view of a retractor extending through a cannula and mounted on the end of a separate shaft.

When the bladder of the retractor is expanded inside the body, it retracts tissue. As seen in FIG. 17, a bladder 522 is mounted on the end of a separate shaft 524 within a cannula or scope 526. The cannula or scope 526 has been inserted into the body through an opening 528 in the skin (either pre-existing or made in situ) which has a transverse dimension 530. The bladder 522 when in its unexpanded condition as shown in broken line is smaller than the dimension 530 of the body opening, but when expanded, it expands to a dimension 532 which is significantly greater than the dimension 530. An actual space or working space 534 is formed which was not present before the expansion of the bladder.

Figure 18:
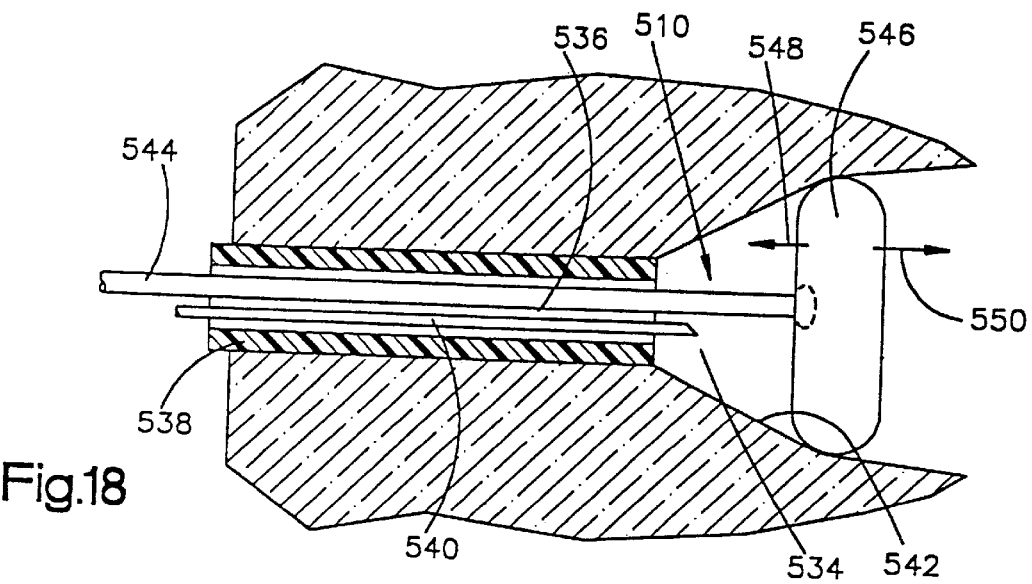
FIG. 18 is a schematic view similar to FIG. 17 illustrating the use of a fiber optic scope with the retractor.

The newly-formed working space may be used, for example, for better use of a fiber optic scope as illustrated in FIG. 3. In FIG. 18, a retractor 510 is passed through an opening 536 in a cannula 538. A fiber optic scope shown schematically at 540 is also passed through the cannula 538. The cannula 538 is inserted into the body through an opening in the body tissues 542 which is only as large as the outer diameter of the cannula 538. The retractor 510 is then inflated, with air or another fluid being supplied through a rigid or flexible shaft 544 to an expandable bladder 546. The bladder 546 expands transversely, retracting the tissues 542 transversely and creating a working space 534. By axial manipulation of the shaft 544, the bladder 546 is movable either toward the end of the scope 540 in the direction as indicated by the arrow 548, or away from the end of the scope 540 as indicated by the arrow 550, as desired. Such manipulation of the retractor can selectively move and place the adjoining body tissues where the surgeon wants them to enable better use of the scope 540 by the surgeon.

Figure 19:
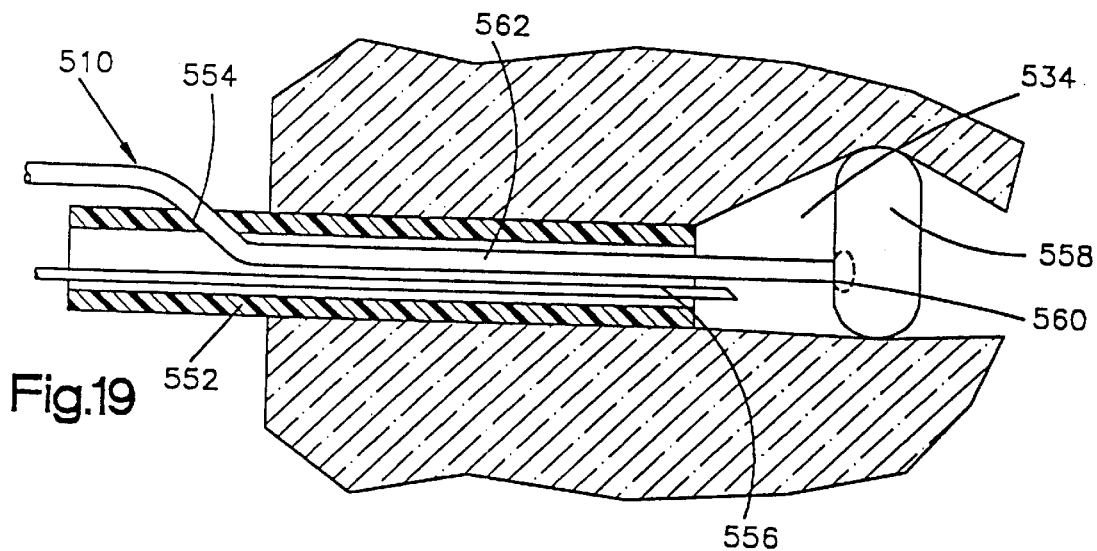
FIG. 19 is a schematic view showing a retractor inserted through a separate side opening in a cannula.
Figures 20A, 20B, 20C, 20D, 20E:
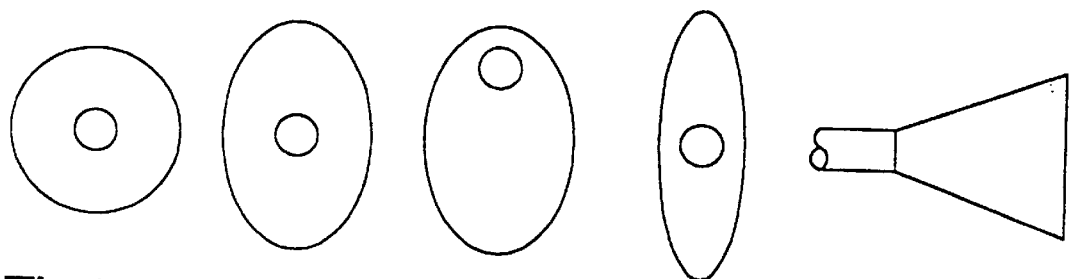
FIGS. 20A–E are schematic views of a few of the many and various shapes in which the inflatable portion of the retractor may be formed.

As shown in FIG. 19, the retractor 510 may be inserted into a cannula 552 through a separate opening 554 therein. The opening 554 is shown on the side of the cannula 552, although, of course, it may be on the end of the cannula as is typical. Alternatively, the retractor 510 may be inserted into the body through an opening in the body tissues separate from the opening through which the fiber optic scope is inserted. Either of these options allows for greater flexibility in the insertion and positioning of the retractor 510 relative to the other instruments being used such as the arthroscope.

Also as indicated in FIG. 19, the bladder 558 may be eccentric or eccentrically located relative to the opening 560 at the junction between the bladder 558 and the shaft 562. This is accomplished by using known techniques to form the bladder 558 of a material, construction, and shape such that it expands into the eccentric shape as illustrated in FIG. 19 when inflated by fluid under pressure through the shaft 562. In this manner, an improved visualization and working space 534 is created which is eccentrically located relative to the other instruments being used. This may be preferable when the surgeon is using an angled scope.

FIG. 19 is illustrative of the fact that the bladder of the retractor of the present invention may be formed so as to expand into any particular shape as desired for the particular application. This feature is also shown schematically in FIGS. 20A through 20E which illustrate, respectively, retractor bladders which assume in their expanded states in round, oval, eccentric, oblong, and conical shapes. Such shapes may generally be called "nonuniform" shapes for purposes of the present invention, and retractors with such a shape will expand in a "non-uniform" manner. Such shapes may include, for example, wedge- or U-shaped filaments which collapse at the skin, then expand at deep tissue planes for visualization and working space. The bladder may also cup and protect vital tissues such as nerves and arteries while working on other tissues such as muscle.

Figure 21:
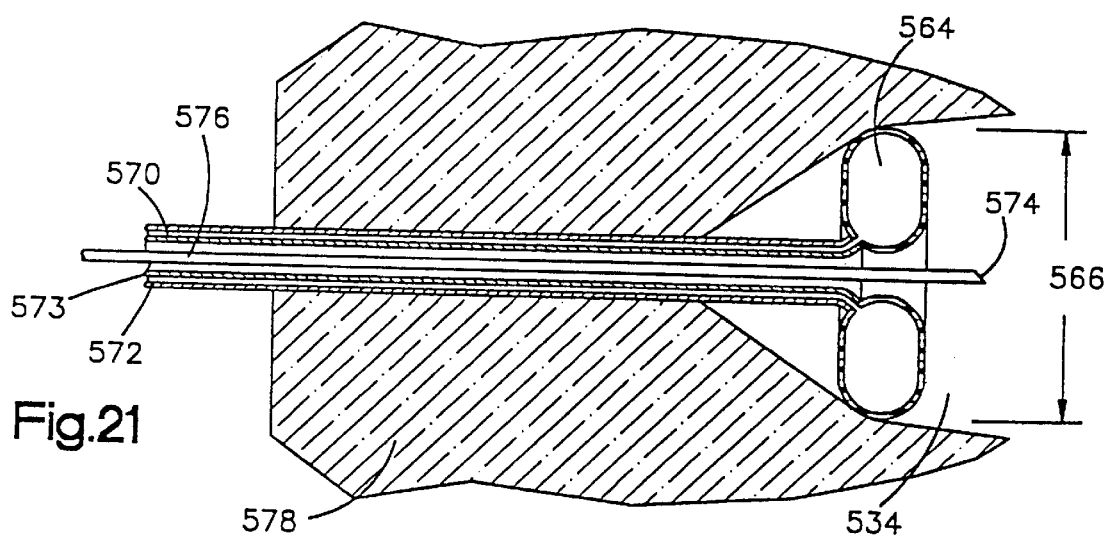

Another typical form of construction is illustrated in FIG. 21, which shows a bladder 564 which in its expanded condition assumes a toroidal shape. Again, the width 566 of the bladder 564 is significantly greater than its length 568. The bladder 568 is expanded by fluid under pressure received through a fluid channel 570 formed between a cannula or scope outer wall 572 and inner wall 573. By virtue of the toroidal shape of the bladder 568, the leading end 574 of the scope 576 may be passed axially completely through the retractor into the working space 534 which has been created in the tissues 578. Such a bladder 564 may also be mounted on a separate shaft inserted through the scope of the cannula.

Figure 22:
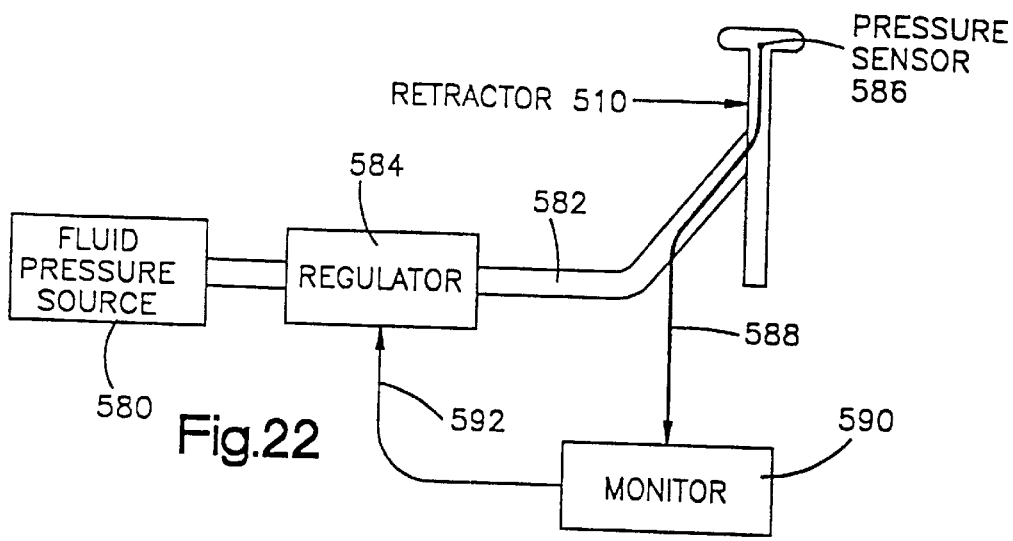
FIG. 22 is a diagram of a fluid supply system for operating a retractor.

In all cases, the fluid pressure within the bladder of the retractor is monitored and controlled to keep the force exerted by the retractor at a safe level for tissue to prevent tissue necrosis. As indicated schematically in FIG. 22, a retractor 510 is supplied with fluid under pressure from a fluid pressure source 580 via a fluid supply line 582. A regulator 584 controls the supply of fluid to the retractor 510. A pressure sensor 586 is located within the retractor 510 and senses the pressure of the fluid within the retractor 510. The pressure sensor 586 sends a signal which is representative of the fluid pressure within the retractor 510, via wiring 588, to a monitor 590. The monitor 590 is connected via control wiring 592 to the pressure regulator 584. The pressure of the fluid within the retractor 510 may thus be monitored and controlled either manually or automatically, by means which are well known in the art and so need not be described further herein. The source 580 of fluid supply may be, for example, the air pressure supply which is commonly found in hospital operating rooms.

By virtue of this ability to monitor the pressure within the retractor 510, the retractor 510 can also be a useful diagnostic tool. The strength or pressure or resistance of tissue to movement can be measured by the pressure required to move it.

Figure 23:
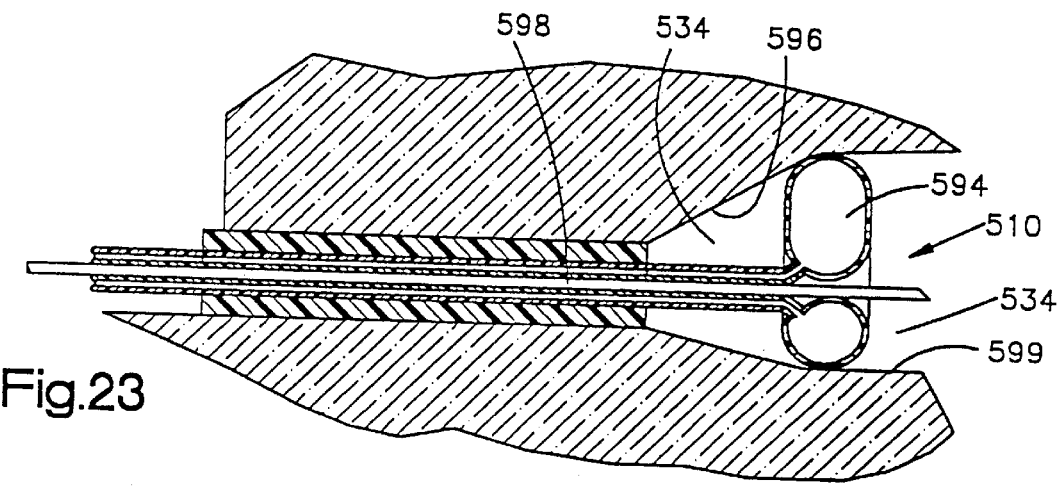
FIG. 23 is a view illustrating the use of a retractor to position the end of a scope.
Figure 24:
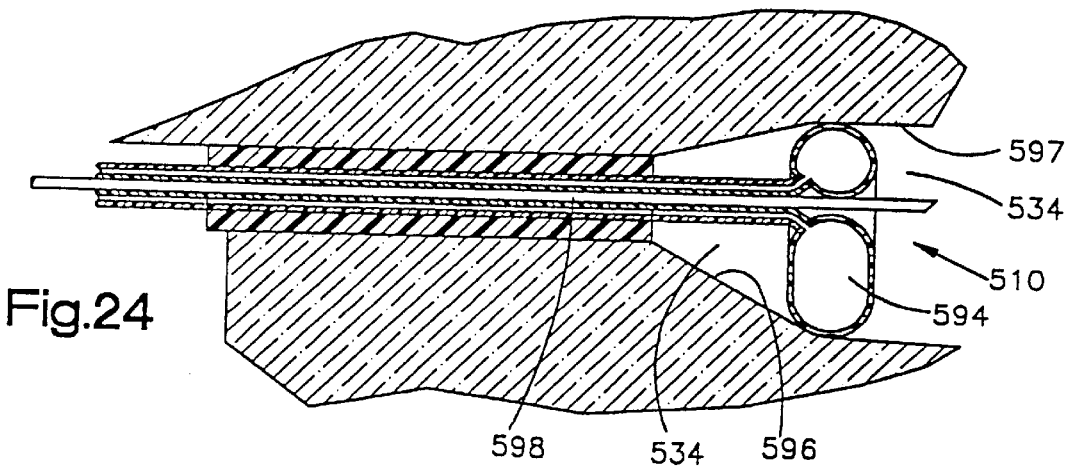
FIG. 24 is a view similar to FIG. 23 further illustrating the use of a retractor to position the end of a scope.

FIGS. 23 and 24 illustrate the use of a retractor of the present invention to stabilize a fiber optic scope. The retractor 510 (FIG. 23) includes a bladder 594 which retracts the body tissues 596 away from the scope 598. Since the bladder 594 engages and pushes radially outwardly on body tissues 596 all around the scope 598, the retractor becomes fixed in position when it is so expanded. If the bladder 594 is fixed to the end of the scope 598, the retractor 510 thereby fixes the end of the scope 598 in position relative to the body tissues 596. When a camera is being used with the scope 598, the picture normally moves or jumps around because of the movability of the end of the scope 598. This is prevented by so using the retractor 510 to stabilize the scope 598, leaving the surgeon with both hands free to work and a steady view of the work area.

FIGS. 23 and 24 also illustrate how the retractor of the present invention can be used to control the placement of the tip of a fiber optic scope. The retractor 510 is formed with an eccentric bladder 594 which retracts the body tissues 596 away from the scope 598 to a greater distance in one direction than in another. Thus, by rotating the retractor 510, the surgeon can place the tip of the scope 596 closer to the body tissue 599 (FIG. 23) on one side of the working space 534, or to the body tissue 597 (FIG. 24) on the other side of the working space 534. Such variable placement can, of course, also be attained via use of a retractor 510 which includes a bladder which can be expanded to varying shapes.

The retractor of the present invention has many uses in the surgical field. The retractor 510 can be used to retract soft tissue from bone, for example within a joint. The retractor 510 is inserted between the bone and the soft tissue 112. The bladder 594 is then expanded. The soft tissue is forced away from the bone. The surgeon may then use a fiber optic scope or other instrument to work within the working space created by the retractor 510. The retractor of the present invention can provide the force needed to move the soft tissue away from the bone may vary between about 100 and 1000 mm Hg, and thus, it is important to maintain the proper pressure between the two. The retractor 510 can do this since it operates on high fluid pressures of about 10 to 1000 mm Hg and it utilizes a high strength material such as Kevlar, Mylar, or another durable polymer such as Polylite®, a product of Reichhold Chemicals, Inc. This simple retraction of soft tissue from bone would otherwise be impossible.

Figure 25:
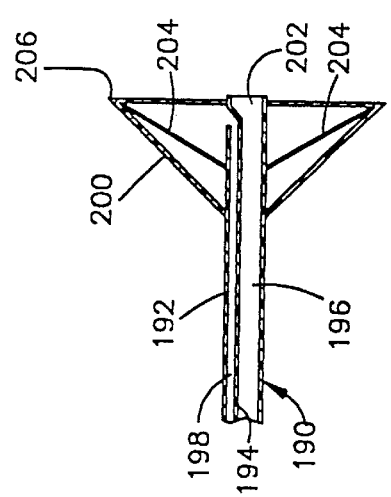
FIG. 25 illustrates a cannula having a tethering cord connecting a balloon portion to the cannula wall.

FIG. 25 illustrates the use of a tethering cord to position a bladder portion relative to a cannula wall. A cannula 190 has a main section with an outer wall 192 and an inner wall 194 spaced therefrom. The wall 194 divides the interior of the cannula 190 into a working passage 196 and an inflation fluid passage 198. The passage 198 opens into a bladder or flexible wall 200 fixed at the distal end 202 of the cannula 190. Tethering cords 204 extend between the cannula wall 192 and a junction or crown 206 of the bladder or flexible wall 200. The tethering cords 204 limit movement of the crown portion 206 of the bladder or flexible wall 200 from the cannula wall 192.

The cannula 190 of FIG. 25 is only illustrative of the many ways in which bladder portions can be positioned relative to cannula portions by tethering cords such as the tethering cord 204. The number and positioning and length of the tethering cords determines the relative movement of the various bladder portions to which they are attached, thus aiding in controlling the expanded shape of the bladder relative to the cannula.

Figure 26:
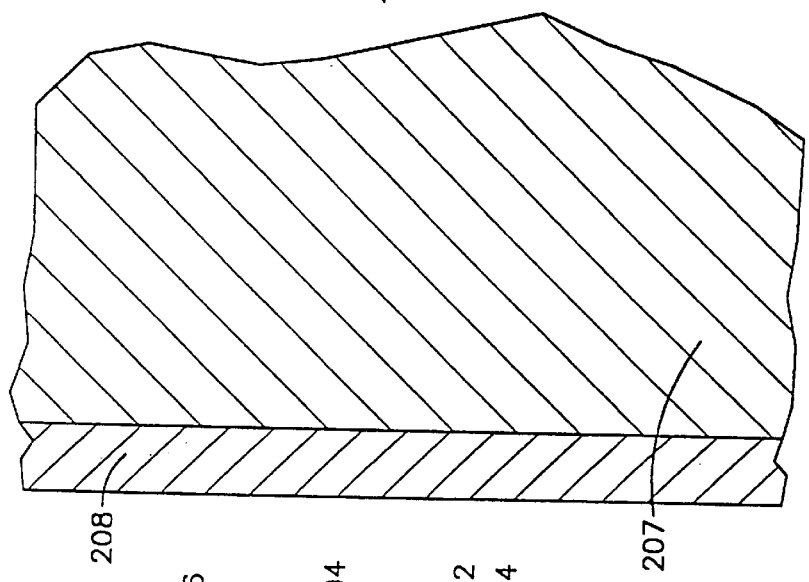
FIG. 26 is a sectional view illustrating a continuous mass of body tissue which is free of an opening.

The cannula 190 can be used to create an open space in a continuous mass of body tissue. Thus, a continuous mass 207 (FIG. 26) of body tissue is free of naturally occurring openings. The mass 207 of body tissue is enclosed by skin 208. The skin 208, like the mass 207 of body tissue, is free of naturally occurring openings.

Figure 27:
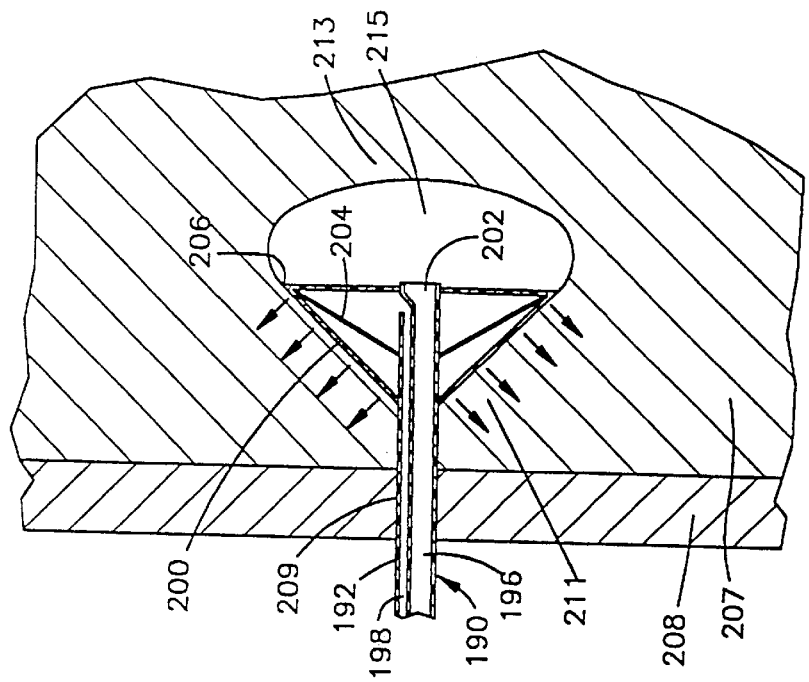
FIG. 27 is a schematic illustration depicting the manner in which the cannula of FIG. 25 is inserted into the mass of body tissue of FIG. 26 and expanded to form an open space in the mass of body tissue at a location adjacent to and axially outward from a distal end of the cannula.

A small slit or incision 209 (FIG. 27) is formed by a surgeon in the skin 208. The cannula 190 is then inserted through the slit 209 in the skin 208. At this time, the bladder 200 in a retracted condition in which it is tightly disposed against the outer wall or main section 192 of the cannula.

Once the cannula 190 has been inserted through the slit 209 and moved into the mass 207 of body tissue, the bladder or flexible wall 200 is moved from the retracted condition to an extended condition. This is accomplished by a conducting fluid pressure through the passage 198 into the flexible wall 200. The fluid pressure expands the flexible wall 200 from a contracted condition to an extended condition.

As the flexible wall 200 is extended, a portion 211 of the mass 207 of body tissue is moved outward away from the outer wall 192 of the main section of the cannula 190. Thus, as the flexible wall 200 is inflated, an outer side surface of the flexible wall presses against the portion 211 of the mass 207 of body tissue, in the manner indicated schematically by arrows in FIG. 27. This pressure moves at least part of the portion 211 of the mass 207 of body tissue toward the left (as viewed in FIG. 27). As this occurs, force is transmitted from the portion 211 of the mass of body tissue to a portion 213 (FIG. 27) of the mass 207 of body tissue.

The force transmitted through the mass 207 of body tissue to the portion 213 of the body tissue moves the portion 213 of the body tissue away from the distal or axially outer end 202 of the cannula 190. As this occurs, an open space 215 is formed at a location in the mass 207 of body tissue where there was no space prior to insertion of the cannula 190 and expansion of the flexible wall 200.

The portion 213 of the mass 207 of body tissue is moved away from the distal end 202 of the cannula 190 under the influence of force which is transmitted through the mass of body tissue from the portion 211 of the body tissue to the portion 213 of the mass of body tissue. Thus, the outer side surface of the flexible wall 200 is effective to apply force, in the manner indicated by arrows in FIG. 27, against only the portion 211 of the mass 207 of body tissue. Force is transmitted by body tissue from the portion 211 of the mass of body tissue to the portion 213 of the mass 207 of body tissue. The force transmitted through the body tissue moves the portion 213 of the mass 207 of body tissue away from the distal end 202 of the cannula 190 and thereby create the open space 215 in the mass 207 of body tissue.

Creation of the open space 215 in the mass of body tissue provides a viewing area adjacent to the distal end 202 of the cannula 190 for a surgeon to operate. Thus, a endoscope 217 and an operating tool 219 can be inserted through the passage 196 in the cannula 190. The outer or distal ends of the endoscope 217 and operating tool 219 project beyond the distal end 202 of the cannula 190 into the open space 215. This enables a surgeon to view the distal end of the operating tool 219 through the endoscope 217 and to view the portion of the mass 207 of body tissue which is to be operated on with the tool 219. Of course, since the surgeon can view the operations being performed by the tool 219, the work of the surgeon on the body tissue 207 is greatly facilitated.

The flexible wall or bladder 200 of the cannula 190 (FIG. 28) includes a side wall 191 and an end wall 193 which are formed of an elastomeric material. When the cannula 190 is inserted through the incision 209, the natural resilience of the elastic end wall 193 and elastic side wall 191 causes the bladder or flexible wall 200 to tightly enclose the outer wall 192 of the cannula 190. This results in the tethers 204 being enclosed by the bladder or flexible wall 200 and being pressed against the outer wall 192 of the cannula 190.

Figure 28:
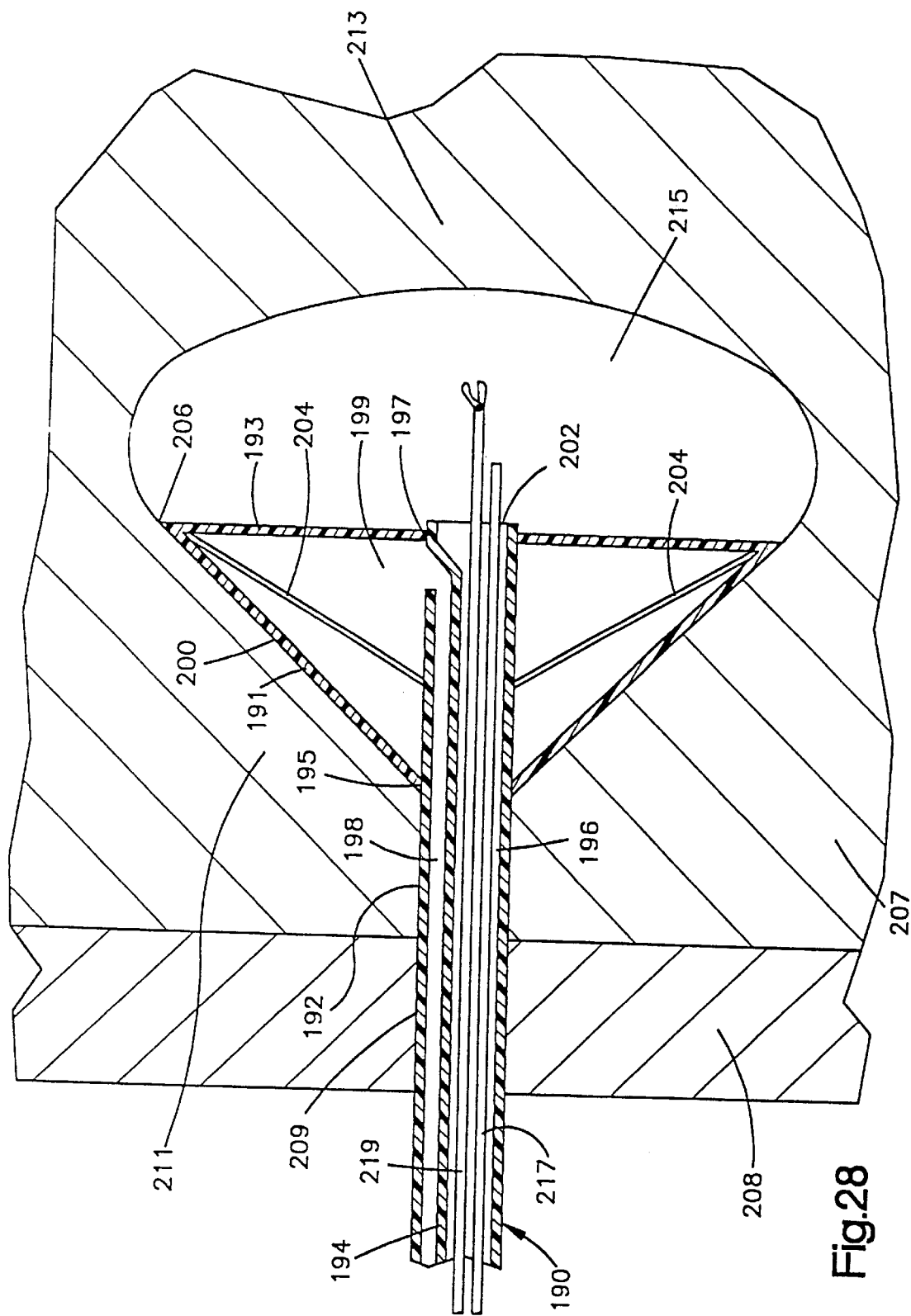
FIG. 28 is an enlarged view of the cannula of FIG. 27 and illustrating the manner in which a fiberoptic scope and a tool are inserted through the cannula into the space formed in the body tissue at a location axially outward from the distal end of the cannula by expanding the cannula.

After the cannula 190 has been inserted through the incision 209 and moved into the continuous mass 207 of body tissue, the bladder 200 is inflated to cause the elastic side wall 191 and end wall 193 of the bladder 200 to move outward to the extended condition shown in FIG. 28. A radially and axially inner end 195 of the side wall 191 of the bladder 200 is bonded to the outer side surface of the outer wall 192 of the cannula 190. A radially inner end of the end wall 193 is bonded at 197 to the outer side surface of the outer wall 192 of the cannula 190. An opening for the fluid passage 198 extends through the outer wall 192 at a location between the connection 195 of the side wall 191 with the outer wall 192 of the cannula 190 and the connection 197 of the end wall 193 with the outer wall 192 of the cannula.

When the bladder or flexible wall 200 (FIG. 28) is to be inflated from the retracted condition to the extended condition shown in FIG. 28, fluid pressure is conducted through the passage 198 into the bladder 200. As the fluid pressure flows into the bladder 200, an annular chamber 199 is established around the outer wall 192 of the cannula 190. As this occurs, the side wall 191 of the bladder 200 presses body tissue radially outward and axially away from the distal end 202 of the cannula 190 in the manner indicated by the arrows in FIG. 27. As this is occurring, the body tissue extends axially outward from the junction 206 between the side wall 191 and end wall 193 of the bladder or flexible wall 200. The body tissue which extends outward from the junction or crown 206 of the bladder 200 is tensioned and tends to continue outward from the junction. Due to the fact that the end wall 193 extends radially outward from the cylindrical outer wall 192 of the cannula 190, an opening is formed immediately axially outward from the end wall 193 as the bladder 200 is inflated.

As the bladder 200 is inflated, the tether cords 204 are extended from a nonlinear configuration toward the linear configuration illustrated in FIG. 28. When the bladder or flexible wall 200 reaches the fully inflated condition shown in FIG. 28, an inflated structure is formed. The tether cords 204 restrain the junction between the side wall 191 and 193 from moving further radially outward. This results in the elastic side wall 191 having a configuration corresponding to the configuration of a portion of a cone and the elastic end wall 193 having a configuration corresponding to the configuration of a flat annular disk. The side wall 191 and end wall 193 are initially formed to this configuration while they are in a stretched condition over a forming tool. The tethering cords 204 cooperate with the side wall 191 and end wall 193 to ensure that the inflated structure formed by the bladder 200 has the configuration illustrated in FIG. 28.

The body tissue 207 which is pressed radially outwardly and axially away from the distal end 202 of the cannula 190 by movement of the bladder 200 from the retracted condition to the expanded condition shown in FIG. 28 causes the body tissue to move away from the end wall 193 as the bladder is inflated. This results in the formation of the open space 215 axially outwardly from the end wall 193. Thus, the portion 211 of the body tissue disposed to the left (as viewed in FIG. 28) of the inflated bladder or flexible wall 200 pulls or tensions the portion of the body tissue which extends across the circular crown portion or junction 206. The forces transmitted through the body tissue itself tends to pull the body tissue away from the end wall 193 to form the open space 215 in the manner illustrated in FIG. 28.

A cannula 600 (FIGS. 29 and 30) has the same general construction as the cannula 190 of FIGS. 25–28. The cannula 600 includes a tubular main section 601 having a cylindrical outer wall 602 which extends from a proximal end portion (not shown) of the cannula 600 to a distal end portion 604 of the cannula. A flexible wall or bladder 606 is connected with the wall 602 of the main section 601. The flexible wall 606 has a proximal end portion 607 which is bonded to an annular shoulder 608 formed in the wall 602. A cylindrical clamp ring 609 also secures the proximal end portion 607 to the wall 602 of the main section 601 of the cannula 600.

A distal end portion 610 of the flexible wall 606 is connected to the distal end of the main section 601 of the cannula 600. In the illustrated embodiment of the invention, the distal end portion 610 of the flexible wall is bonded to the distal end of the main section 601 of the cannula 600. However, the distal end portion 610 of the flexible wall 606 could be connected to the distal end of the main section 601 in other ways, such as by the use of a mechanical retainer. When the flexible wall 606 is in the initial or retracted condition shown in FIG. 29, the flexible wall tightly adheres to the main section 601 of the cannula 600 to provide a smooth outer surface which has a minimum of interference with body tissue as the cannula 600 is inserted into a continuous mass of body tissue.

An inner wall 612 cooperates with the wall 602 to form a passage 614 for fluid. The passage 614 has a proximal end (not shown) at which fluid under pressure is conducted into the passage. The passage 614 has a plurality of circular distal openings 616 through which fluid can flow from the passage 614 to a space enclosed by the flexible wall 606.

When the flexible wall 606 is to be inflated, fluid pressure flows through the passage 614 and opening 616 and is applied against an inner side surface 617 (FIG. 29) of the flexible wall. The fluid pressure applied against the inner side surface 617 of the flexible wall 606 causes the flexible wall to move from the retracted condition shown in FIG. 29 toward the fully extended condition shown in FIG. 30. As this occurs, a plurality of tether cords 618 are pulled from a nonlinear or coiled configuration toward the linear configuration shown in FIGS. 30 and 31.

Figure 29:
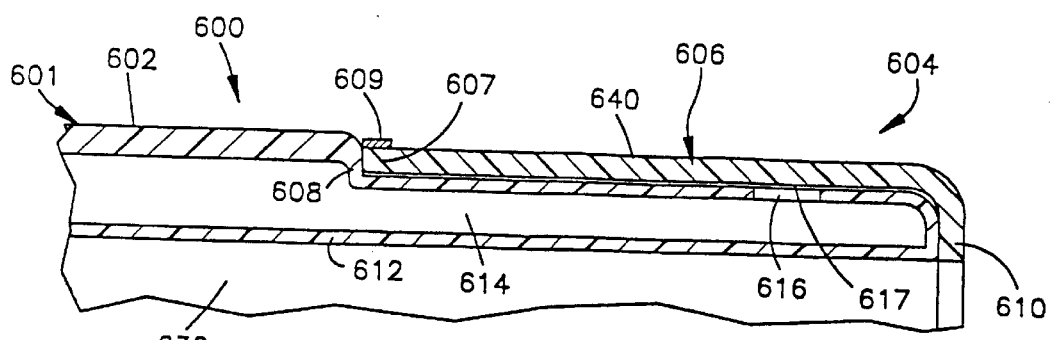
FIG. 29 is an enlarged fragmentary sectional view of a cannula having a flexible wall and tethers, the flexible wall being shown in a retracted condition.

When the flexible wall 606 is in the retracted condition shown in FIG. 29, the flexible wall covers the tethers 618 and presses them firmly against the tubular wall 602 of the main section 601 of the cannula 600. Since the tethers 618 are enclosed by the flexible wall 606, they do not interfere with insertion of the cannula 600 into a continuous mass of body tissue 207 where an opening does not naturally occur. The relatively high pressure fluid conducted from the passage 614 through the openings 616 move the flexible wall 606 outwardly away from the main section 601 of the cannula 600 to initiate the formation of an inflation fluid chamber 620. As this occurs, the flexible wall 606 forms an inflated structure 622.

The inflated structure 622 has a side wall 624 and an end wall 626. The side wall 624 and end wall 626 are connected at a circular junction 628. The side wall 624 has a configuration corresponding to the configuration of a portion of a cone while the end wall 626 has a configuration corresponding to the configuration of a flat annular disk when the flexible wall 606 is in the fully extended position of FIG. 30. The tethering cords 618 limit outward movement of the junction 628 between the side wall 624 and the end wall 626 to impart the desired configuration to the inflated structure 622.

Each of the tethering cords 618 has an outer end portion which is secured to the inner side surface 617 of the flexible wall 606 at the junction 628. In the illustrated embodiment of the invention, the tethering cords 618 are bonded to the elastomeric material forming the flexible wall 606. However, it is contemplated that the tethering cords 618 could be connected with the flexible wall 606 in many different ways. The inner end portions of the tethers 618 are bonded to the main section 601 of the cannula 600. The inner end portions of the tethers 618 could be secured to the main section 601 of the cannula 600 in many different ways other than bonding.

The tethering cords 618 limit radially outward movement of the junction 628 between the end wall 626 and side wall 624. By limiting outward radial movement of the end wall 626 and the side wall 624, the tethering cords 618 restrain the elastic material of the flexible wall 606. This results in the inflated structure 622 having a configuration which corresponds to the configuration of a portion of a cone.

Figure 30:
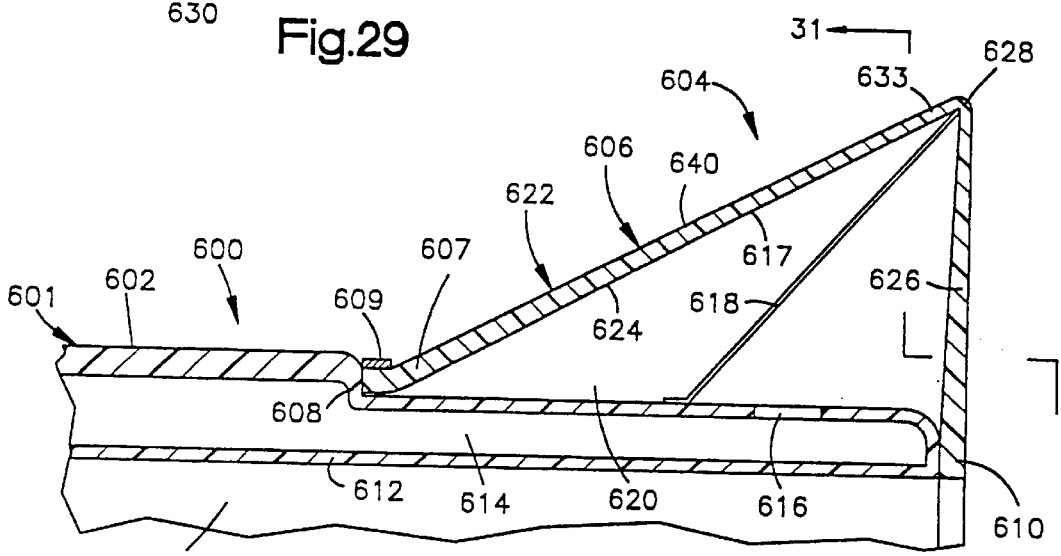
FIG. 30 is a fragmentary sectional view, generally similar to FIG. 29, illustrating the flexible wall in an extended condition with a tether limiting outward movement of a portion of the flexible wall.
Figure 31:
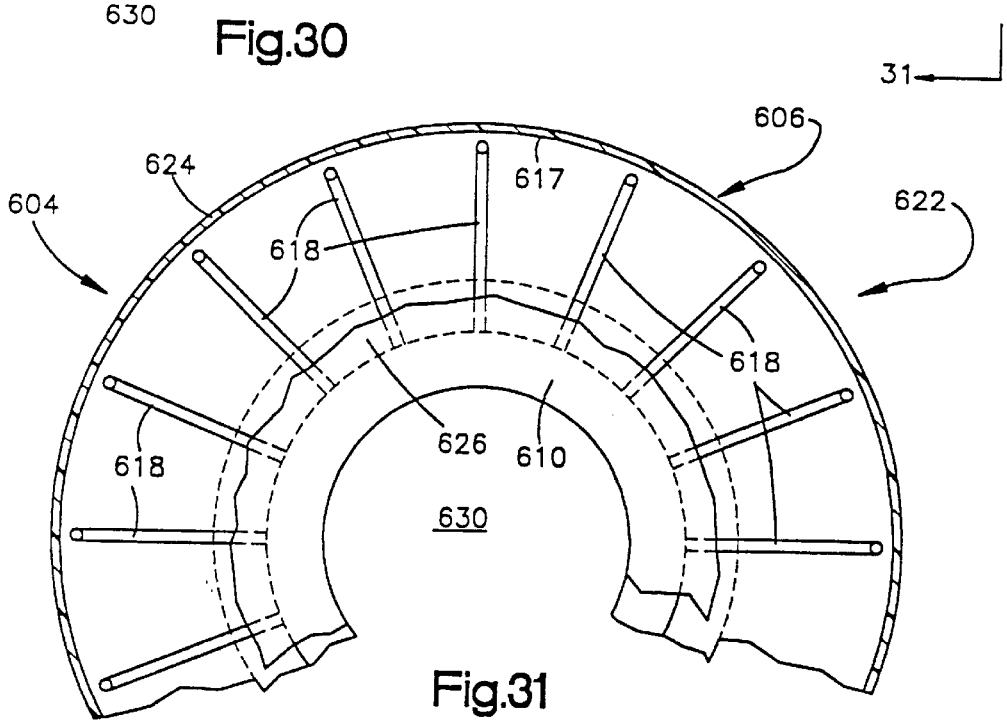
FIG. 31 is a fragmentary sectional distal end view, taken generally along the line 31—31 of FIG. 30, illustrating the manner in which a plurality of tethers extend outwardly from a main section of the cannula toward the flexible wall.
Figure 32:
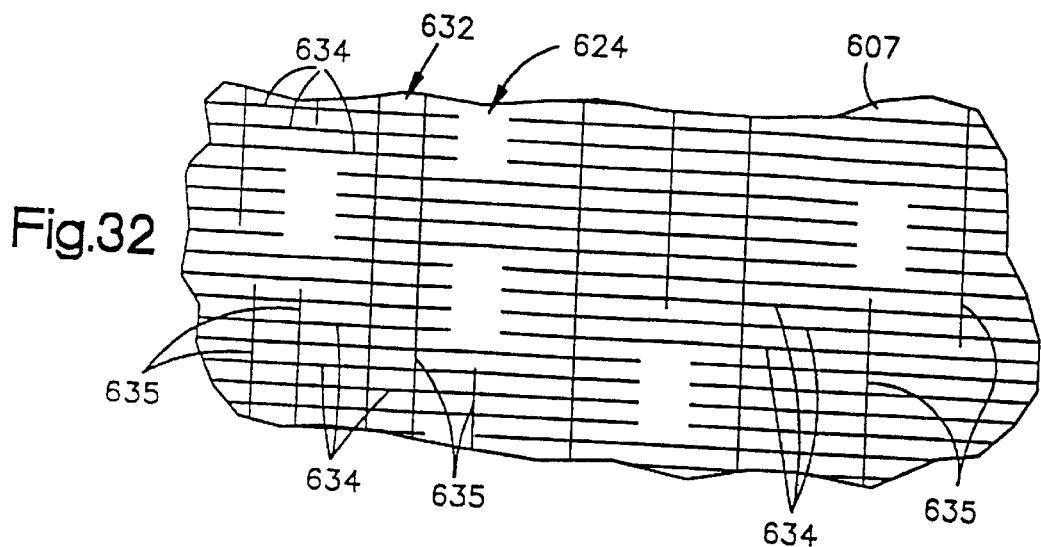
FIG. 32 is a fragmentary schematic plan view of a portion of a side wall of the flexible wall of the cannula of FIGS. 29–31 and schematically illustrating the relationship between reinforcing fibers in a proximal portion of the side wall.
Figure 33:
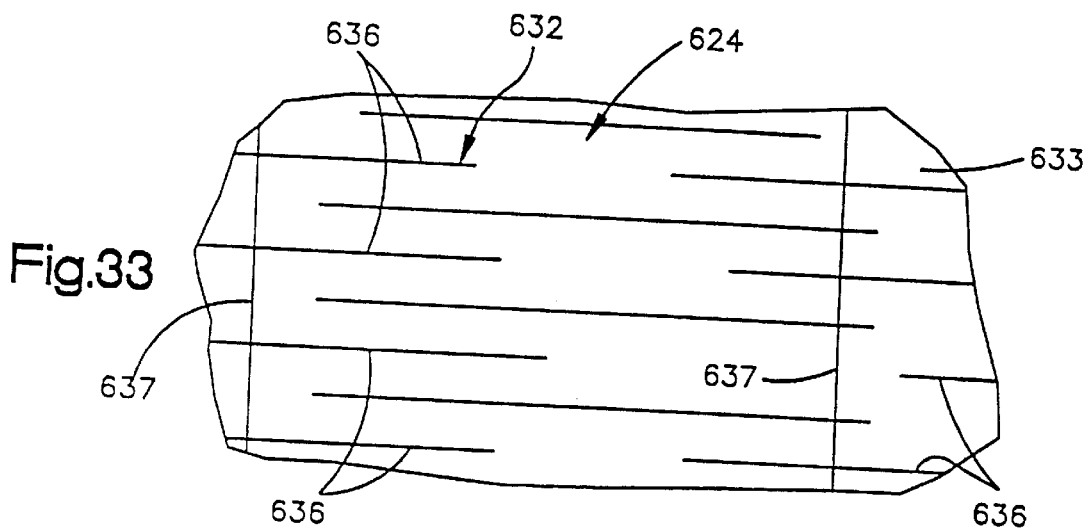
FIG. 33 is a fragmentary plan view of another portion of the side wall of the flexible wall of the cannula of FIGS. 29–31 and schematically illustrating the relationship between reinforcing fibers in a distal portion of the flexible wall.
Figure 34:
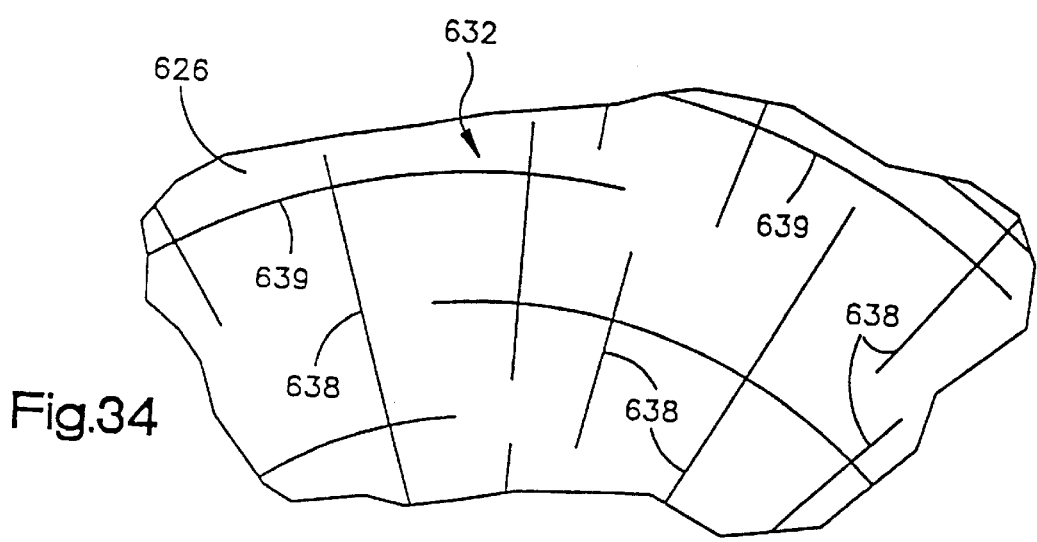
FIG. 34 is a plan view of a portion of an end wall of the flexible wall of FIGS. 29–31 and schematically illustrating the relationship between reinforcing fibers in the end wall.

Once the flexible wall 606 has been moved to the extended condition of FIG. 30, instruments, such as an endoscope and/or operating tools, can be inserted through a cylindrical central opening 630 (FIG. 31) formed in the main section 601 (FIGS. 29 and 30) of the cannula 600. In addition to the tethers 618, reinforcing fibers 632 (FIGS. 32, 33 and 34) are utilized to impart the desired configuration to the inflated structure 622.

A portion of the reinforcing fibers 632 is disposed in the side wall 624 (FIGS. 32 and 33) of the inflated structure 622. Another portion of the reinforcing fibers 632 is disposed in the end wall 626 of the inflated structure 622. The reinforcing fibers 632 cooperate with the elastomeric material, which may be silicone, or latex, to restrain the elastomeric material of the flexible wall 606 against excessive stretching under the influence of fluid pressure applied against the inner side surface 617 (FIGS. 30 and 31) of the flexible wall 606.

In the illustrated embodiment of the invention, the inflated structure 622 has a configuration corresponding to the configuration of a portion of a cone. Therefore, a proximal portion 607 of the side wall 604 has a smaller diameter than a distal end portion 633 of the side wall 624. The density of reinforcing fibers 632 in the proximal end portion 607 (FIG. 32) of the side wall 624 is greater than the density of reinforcing fibers 632 in the distal portion 633 of the side wall 624. By having the reinforcing fibers in the proximal end portion 607 (FIG. 32) of the side wall 624 closer together, the reinforcing fibers are effective to limit outward radial expansion of the proximal portion 607 of the side wall 624. The relatively widely spaced reinforcing fibers 632 (FIG. 23) in the distal end portion 633 of the side wall 624 allow the distal end portion 633 of the side wall 624 to expand radially outwardly to a greater extent than the proximal end portion 607 of the side wall 624.

The reinforcing fibers 632 in the proximal end portion 607 of the side wall 624 (FIG. 32) include fibers 634 having longitudinal axes which extend generally parallel to a longitudinal central axis of the main section 601 of the cannula 600. In addition, reinforcing fibers 635 extend circumferentially around the distal portion 607 of the side wall 624. The reinforcing fibers 635 have longitudinal axes which extend generally perpendicular to the longitudinal axis of the reinforcing fibers 634. The longitudinal extending fibers 634 and the circumferentially extending fibers 635 reinforce the proximal portion 607 of the side wall 624 to limit the extent to which the fluid pressure applied against the inner side surface 617 of the side wall is effective to stretch the elastomeric material of the flexible wall 606.

Similarly, the distal end portion 633 (FIG. 33) of the side wall 624 has longitudinally extending fibers 636 having longitudinal axes which extend parallel to the longitudinal central axis of the main section 601 of the cannula 600. The reinforcing fibers 632 in the distal end portion 633 of the side wall 624 also include circumferentially extending fibers 637 which are perpendicular to the longitudinally extending fibers 636. The reinforcing fibers 632 in the distal portion of the side wall 624 are far more widely spaced than the reinforcing fibers in the proximal end portion 607 of the side wall 624. This enables the elastomeric material of the distal end portion 633 to stretch under the influence of fluid pressure applied against the inner side surface 617 (FIG. 30) of the side wall 624. Therefore, the distal portion 633 of the side wall 624 stretches to have a substantially greater diameter than the proximal portion 607 of the side wall 624.

The reinforcing fibers 632 in the end wall 626 (FIG. 34) include fibers 638 which extend radially outwardly from the cylindrical passage 630 through the main section 601 of the cannula. Circumferentially extending fibers 639 cooperate with the radially extending fibers 638 to limit the expansion of the end wall 626 under the influence of fluid pressure applied against the inner side surface 617 of the flexible wall 606. During formation of the flexible wall 606, the elastomeric material of the flexible wall is configured to have a configuration corresponding to the desired, generally conical, configuration of the inflated structure 622 (FIG. 30).

The cannula 600 is inserted into a continuous mass of body tissue, corresponding to the continuous mass 207 (FIG. 26) of body tissue, with the flexible wall 606 of the cannula 600 in the retracted condition illustrated in FIG. 29. This enables the cannula 600 to be inserted through a relatively small incision formed in the skin enclosing the continuous mass of tissue. Prior to insertion of the cannula 600 into the continuous mass of tissue, the continuous mass of tissue is free of any openings. As the cannula 600 is inserted into the continuous mass of body tissue with the flexible wall 606 in the retracted condition of FIG. 29, the relatively smooth outer side surface of the cannula is effective to press aside the body tissue with a minimum of damage to the tissue.

Once the cannula 600 has been inserted into the continuous mass of body tissue, fluid under pressure is conducted through the passage 614 (FIG. 29) to initiate inflation of the flexible wall 606. As this occurs, the flexible wall 606 begins to move away from the main section 601 of the cannula 600. This results in an outer side surface 640 of the flexible wall 606 pressing against the body tissue to move the body tissue away from the main section 601 of the cannula 600.

As the inflation of the flexible wall 606 continues, the outer side surface 640 of the flexible wall disposed on the conical side wall 624 presses the tissue both radially outwardly and axially away from the distal end of the main section 601 of the cannula 600. As this occurs, force is transmitted through the body tissue itself to pull the body tissue away from the end wall 626 and the distal or axially outer end of the cannula 600 to initiate the formation of an open space immediately axially outwardly of the end wall 626.

As the flexible wall 606 continues to move away from the retracted condition of FIG. 29 toward the fully extended condition of FIG. 30, the tethers 618 are straightened. When the flexible wall 606 reaches the fully extended condition of FIG. 30, the tethers 618 limit outward movement of the junction 628 between the end wall 626 and side wall 624. Thus, force is transmitted through the tethers 618 from the junction 628 to the main section 601 of the cannula 600 to limit outward movement of the junction 628. The reinforcing fibers 632 (FIGS. 32, 33 and 34), cooperate with the tethers 618 to give the side wall 624 the conical configuration shown in FIG. 30 and the end wall 626 a flat annular disk-shaped configuration.

Figure 35:
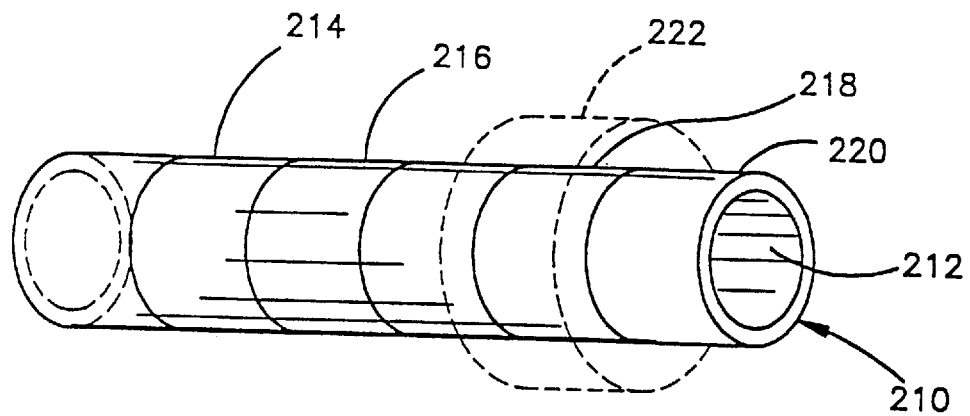
FIG. 35 illustrates a cannula which is selectively expandable at one or more selected longitudinal locations.

FIG. 35 illustrates a cannula 210 which is selectively expandable at one or more selected longitudinal locations. The cannula 210 includes a series of expandable wall segments defining a longitudinally extending central working passage 212. The expandable segments illustrated include a segment 214, a segment 216, a segment 218, and a segment 220. As an example, the segment 218 is expandable, upon the introduction of fluid under pressure, to an expanded condition as illustrated at 222 in FIG. 35. Thus, in accordance with the principles illustrated in FIG. 35, a cannula or other inflatable medical device can be expanded for positioning or sealing at one or more selected longitudinal locations.

Figures 36, 37:
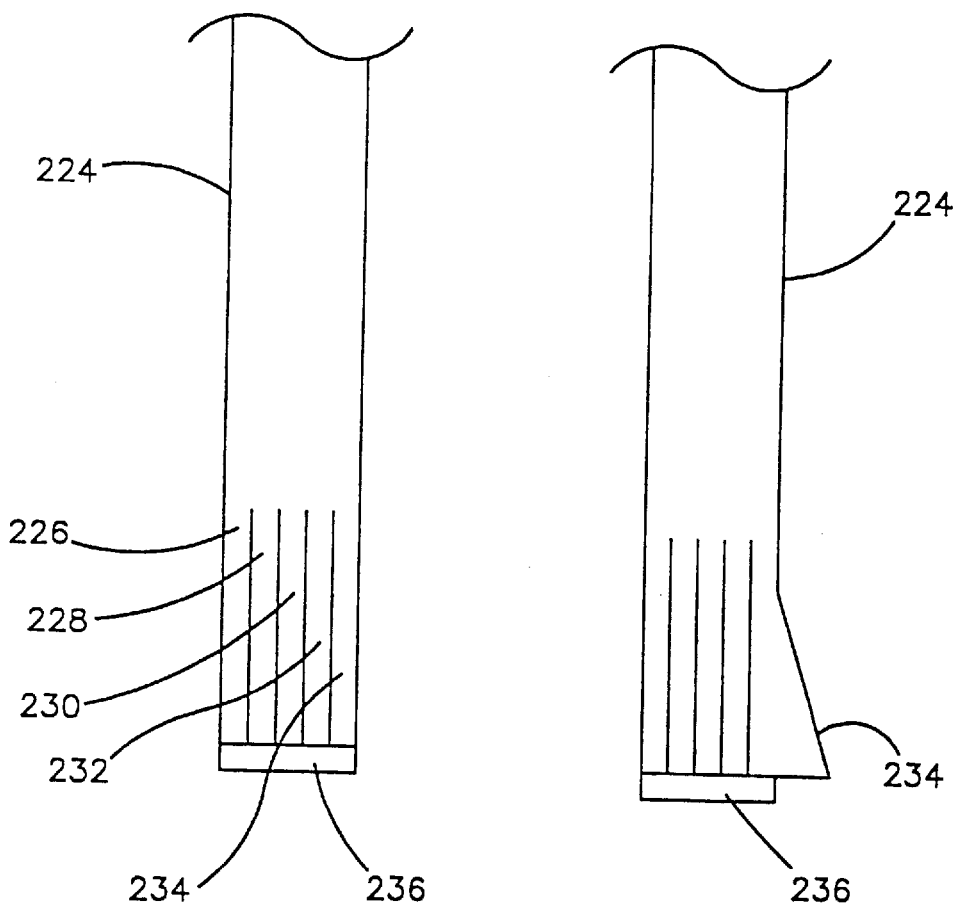
FIGS. 36 and 37 illustrate a cannula having a plurality of circumferentially spaced expandable segments.

FIG. 36 similarly illustrates a cannula 224 having a plurality of expandable segments 226 through 234 spaced circumferentially around the distal end portion 236 of the cannula 224. Each of the segments 226–234 is selectively expandable, as illustrated in FIG. 37 showing the segment 234 expanded radially outwardly. Accordingly, it is seen that the present invention also contemplates a cannula or bladder, or other inflatable medical device, having a plurality of circumferentially disposed segments expandable radially outwardly upon the selective control of the user of the device. Such selective expansion is useful in selectively positioning the cannula within the tissue in which it is located, in avoiding damage to certain tissue such as nerve tissue, or in protecting or moving certain tissue selectively.

FIGS. 38–43 illustrate such longitudinally extending radially expansible segments of a cannula or bladder or other inflatable medical device in accordance with the present invention. Each segment shown is one of a series of similar segments (not shown) spaced circumferentially around or formed as part of the wall of a cannula or other device 250. The expansible segment 240 illustrated in FIGS. 38–43 is formed as a bellows or accordion and is expandable to a larger extent at its distal end 244 than at its proximal end 242. If the distal end 244 of the expansible segment 240 is located adjacent a distal end of a cannula, the cannula will thus be expandable directly at its tip. The bellows-like construction of the segment 240 provides significant structural rigidity and can transmit in a controlled manner a significant amount of force between its radially outer surface 246 and its radially inner surface 248 adjacent the wall of the cannula 250. The segment 240 is inflated by introduction of fluid under pressure in a known manner into the inflation space 252 (FIG. 41).

The expandable segment 254 illustrated in FIGS. 42 and 43 has a smooth outer skin 256 supported by a plurality of expandable bellows-shaped hoops 258 spaced longitudinally along the length of the segment 254. The skin 256 presents a smooth surface to adjoining tissues upon expansion of the segment 254. The hoops 258 provide structural rigidity to the segment 254, and control the shape of expansion of the skin 256. It should be understood that other configurations of the hoops 258, which support the skin 256 of the segment 254, are contemplated.

Figure 45:
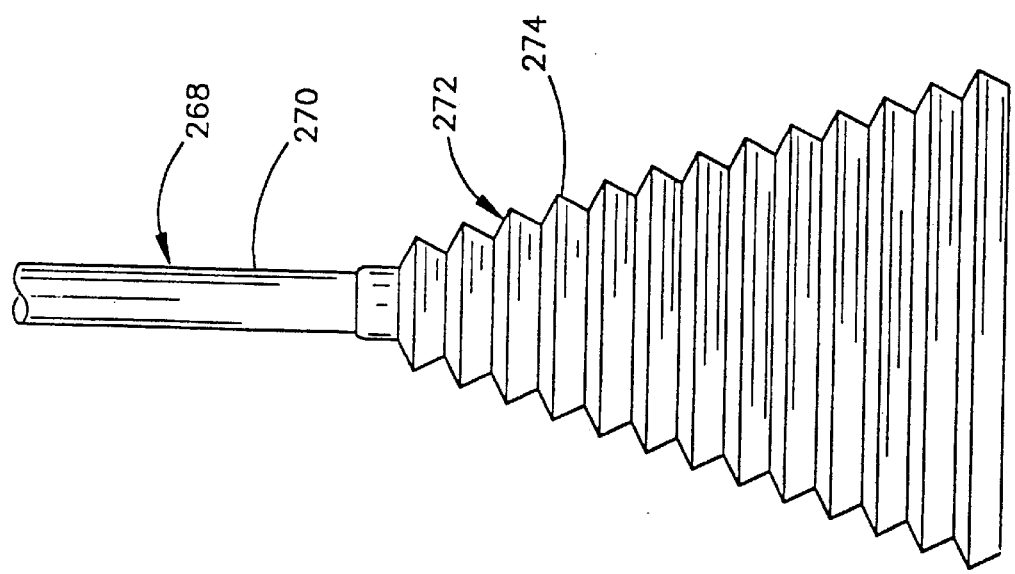
FIGS. 44 and 45 illustrate expandable devices having textured surfaces.
Figure 44:
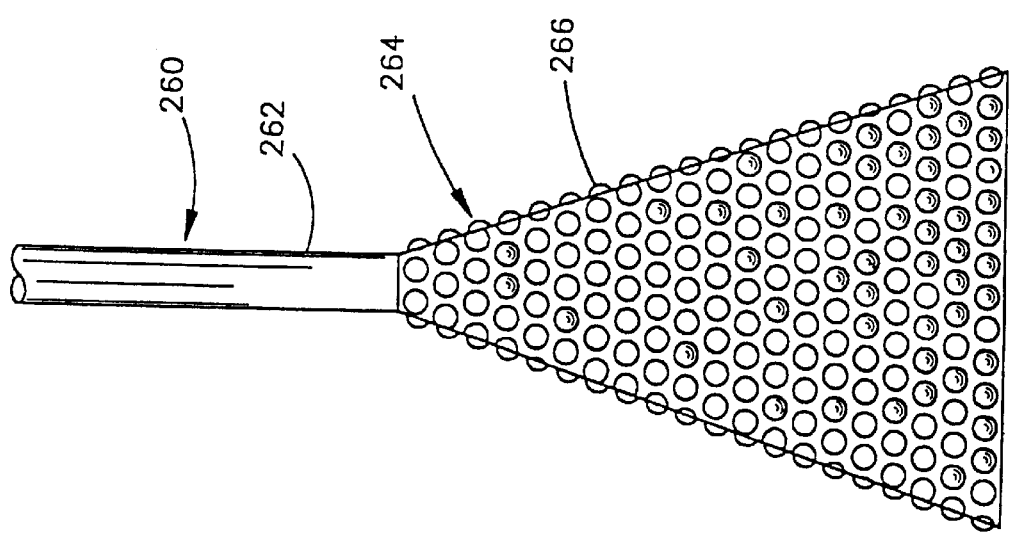

FIGS. 44 and 45 illustrate expandable devices having textured surfaces for grip and location control. The retractor 260 illustrated in FIG. 44 includes a stalk portion 262 and a bladder portion 264 attached thereto. The bladder portion 264 has a pebbled surface 266. The retractor 268 (FIG. 45) has a stalk portion 270 and a bladder portion 272. The bladder 272 has a ribbed surface 274. Other types of texturing or finishing may be provided for an expandable device in accordance with the present invention. Any suitable surface configuration may be used to increase the grip provided between the outer surface of the expandable device and the tissue which it contacts. It should be noted that the surface texturing may also increase the structural rigidity of the expanded device.

FIGS. 46–49 illustrate an expanding device 280 which is preshaped and has a varying wall thickness in its expanding bladder portion. The expanding device 280 includes a support member 282 which may be a solid stalk or a hollow cannula or other member. The support member 282 has a widened proximal portion 286, a narrower diameter central portion 288, and a widened distal portion 290.

Bonded to the support member 282 is an expanding bladder 292. The expanding bladder 292 includes a proximal portion 294 bonded to the proximal portion 286 of the support member 282. The expanding bladder 292 also includes a distal portion 296 bonded to the distal end portion 290 of the support member 282. Extending distally from the portion 294 is a first expanding portion 298 having a thinner wall section at its proximal end 300 and a thicker wall section at its distal end 302. Extending distally from the expanding portion 298 to the thin wall portion 296 is a second expanding portion 304. The second expanding portion 304 is thicker at its proximal end 306 than at its distal end 308, having a tapering cross section between the first expanding portion 298 and the distal end portion 296.

When in the unexpanded condition, the first and second expanding portions 298 and 304, respectively, of the expandable bladder 292 generally lie flat within the recess formed by the narrow portion 288 of the support member 282. Upon the introduction of fluid under pressure into the interior of the bladder 292 through a port (not shown) in the support member 282, the bladder 292 expands from the condition illustrated in FIG. 46 to the condition illustrated in FIG. 47. The expanding portions 298 and 304 expand radially outwardly as illustrated. Because the material of the bladder 292 is thinner at its axially outer end portions 300 and 308, that material stretches more and so the thicker portions 302 and 306 move radially outwardly the greatest amount. The proximal and distal end portions 294 and 296, respectively, are prestretched, that is, stretched to a diameter greater than their relaxed condition, for insertion over the support member 282.

Thus, it is seen that the wall thickness of a bladder can be varied at selected locations to control the rates and distances of expansion of the bladder portions. Further, portions of the bladder can be prestretched so that they reach their maximum elongation at an earlier amount of expansion. These factors can be used to control the expanded shape of the bladder.

In addition, there may be provided ribs such as the longitudinally extending ribs 310 illustrated in FIGS. 48 and 49 which are of an increased wall thickness to provide structural support and expansion control of the elastomeric material of the bladder. The ribs 310 are illustrative of any region of increased wall thickness used to control the shape of expansion. Such regions may run longitudinally as illustrated in the device 280, or may run transversely or circumferentially or in other directions. Taken in combination, all of these factors are usable to control the shape of expansion of an inflatable medical device.

In accordance with a further embodiment of the invention, relatively rigid members such as plates may be molded into relatively flexible bladder portions to define edges and surfaces, as illustrated in FIGS. 50–52. A medical device 312 (FIG. 50) includes a support member 314 such as a cannula to which is attached an expanding (elastomeric) bladder 316. The attachment between the bladder 316 and the support member 314 is not shown in these particular cross-sectional views, but may be in any manner known or as described herein. The bladder 316 has an elastomeric curved portion 318 and an elastomeric portion 319. A plate 320 is molded into the bladder 316 and has an edge 322. A second plate 324 molded into the bladder 316 has an edge 326. Upon the introduction of fluid under pressure into the volume between the support member 314 and the bladder 316, the bladder expands radially outwardly from the condition shown in FIG. 50 to the condition shown in FIG. 51. Although the elastomeric portion 318 of the bladder 316 changes dimensions, the plates 320 and 324 do not. Thus, the expanding device 316 includes flat surfaces and edge surfaces which move radially outwardly and maintain their rigid condition upon expansion of the device 312. The plates 320 and 324 thus control and partially define the expanded shape of the device 312.

Alternatively or additionally, as illustrated in FIG. 52, tethering cords 328 may be employed between the support member 314 and the plates 320 and 324. The tethering cords 328 also serve to control and/or limit expansion of the device 312. Additionally, it can be seen that the device of FIG. 52 includes elastomeric bladder portions 330 extending directly between the plates 320 and 324 and the support member 314. Again, this is an alternative form of the construction. Expanding bladders constructed in accordance with the present invention can use any one or more of these various means of controlling or limiting the expansion of the inflatable medical device, in order to achieve the optimum structure for the particular application.

FIGS. 53 and 54 further illustrate the use of rigid plates or members molded into elastomeric material of an inflatable medical device. An expanding bladder 332 is fixed circumferentially by means not shown around a cannula 334. The cannula 334 includes a cannula wall 336 defining a longitudinally extending central opening 338. The expanding bladder 332 includes an elastomeric material 340 within which are molded a series of relatively rigid plates 342. Between the expanding bladder 332 and the cannula wall 336 is a fluid inflation space 344. Upon the introduction of fluid under pressure into the inflation volume 344, the expanding bladder 332 expands radially outwardly from the condition shown in FIG. 53 to the condition shown in FIG. 54. The elastomeric material 340 stretches and elongates circumferentially. The areas of the elastomeric material 340 which are devoid of plates 342 stretch further, thus allowing the plates 342 to separate. The plates 342, which were previously in overlapping position, are separated as illustrated in FIG. 54. The plates 342 impart structural rigidity and strength to the elastomeric material 340. The invention is not limited to the particular configuration of rigid plates and elastomeric material illustrated, but contemplates any such configuration of relatively rigid members or portions in a relatively stretchable matrix material.

Figure 55:
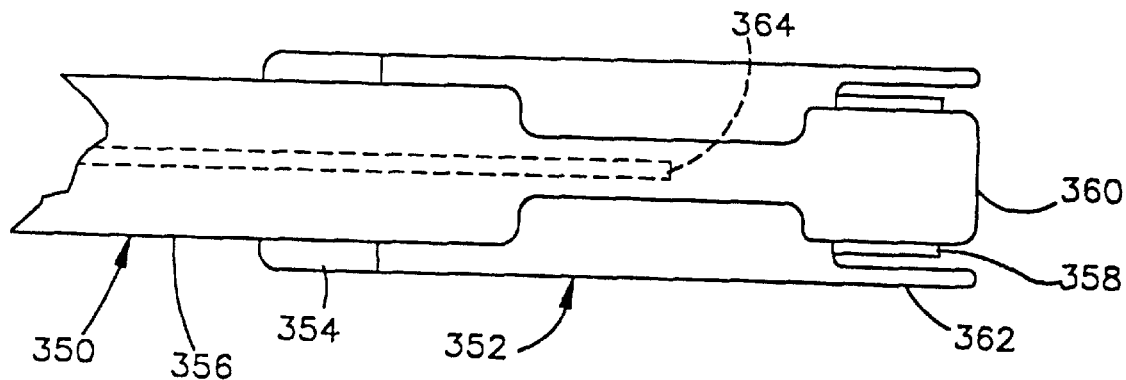
FIGS. 55 and 56 illustrate a cannula having a bladder with a doubled-over bladder portion.
Figure 56:
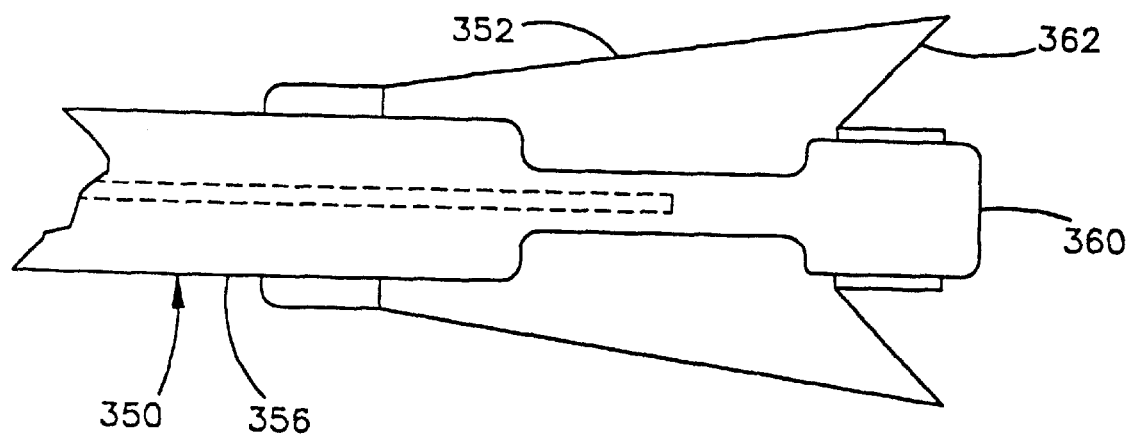

The expanding device illustrated in FIGS. 55 and 56 includes a doubled-over bladder portion to allow maximum expansion at the distal end portion of the device. The device includes a cannula or stalk or other support member 350. An expanding bladder 352 is bonded at 354 to a proximal portion 356 of the support member 350, and at 358 to a distal end portion 360 of the support member 350. The material of the expanding bladder 352 is doubled-over at 362 adjacent the distal end portion 360. Upon the introduction of fluid under pressure into the volume defined by the bladder 352, through a fluid supply port 364, the bladder 352 expands from the condition shown in FIG. 55 to the condition shown in FIG. 56. Because of the doubled-over portion 362 of the bladder 352, maximum expansion is gained at the distal end of the device rather than at the center or the proximal end of the expanding bladder 352. Again, such a device may include bladder portions having varying wall thicknesses as discussed above, tethering cords, etc., all to control the expanded shape of the device.

The expanding device illustrated in FIGS. 57 through 62 includes a doubled-over bladder portion to allow maximum expansion at the distal end portion of the device in the manner previously described in connection with FIGS. 55 and 56. The device includes a cannula having a main section or stalk 850. An expanding bladder or flexible wall 852 is bonded at 854 to a proximal end portion 856 of the support member 850 and at 858 to a distal end portion 860 of the main section 850 (FIGS. 57 and 58). The material of the expanding bladder 852 is doubled-over at 862 adjacent to the distal end portion 860.

Upon introduction of fluid under pressure into the volume defined by the bladder 852, through a fluid supply port 864 (FIG. 57), the bladder or flexible wall 852 expands from the condition shown in FIG. 57 to the condition shown in FIG. 58. Because of the doubled-over portion 862 of the bladder 852, maximum expansion is gained at the distal end of the device rather than at the center or proximal end of the expanding bladder 852. Again, such a device may include bladder portions having varying wall thicknesses as discussed above or reinforcing fibers to control the expanded shape of the device.

In the embodiment illustrated in FIGS. 57 and 58, tethering cords 870 extend from the main section 850 of the cannula to a junction 872 between a side wall 874 and an end wall 876 (FIG. 58) of the flexible wall or bladder 852. The tethering cords 870 limit the extent of outward movement of the junction 872 when the flexible wall or bladder 852 is inflated from the retracted condition of FIG. 57 to the extended condition of FIG. 58. The side wall 874 of the inflated flexible wall has a configuration corresponding to the configuration of a portion of a cone. The end wall 876 has a configuration corresponding to the configuration of an annular disk. However, it should be understood that the end wall 876 slopes radially and axially outwardly from a location where the side wall 876 is connected with the main section 850 of the cannula to the-junction 872 between the end wall and the side wall 874.

In accordance with a feature of this embodiment of the invention, tethering cords 870 extend outwardly from the distal end portion of the main section 850 to the junction 872 between the side wall 874 and end wall 876. The tethering cords 870 limit outward movement of the flexible wall or bladder 852 to assist in imparting the desired configuration to the bladder when it is in the expanded condition of FIG. 58. Although only a pair of tethering cords 870 are shown in FIGS. 57 and 58, it should be understood that there is a circular outer array 880 of tethering cords which extend from the main section 850 of the cannula outwardly to the junction 872. Although any desired number of tethering cords could be used, in the illustrated embodiment of the invention, there are nine tethering cords in the circular array 880 of tethering cords.

In the embodiment of the invention illustrated in FIGS. 59–62, the cannula has the same general construction as the cannula of FIGS. 57 and 58. However, in the embodiment of the invention illustrated in FIGS. 59–62, tethering cords are provided between an inner side surface of the side wall 874 of the bladder or flexible wall and the main section 850 of the cannula. Since the embodiment of the invention illustrated in FIGS. 59–62 is generally similar to the embodiment of the invention illustrated in FIGS. 57 and 58, similar numerals have been utilized to designate similar components.

In accordance with a feature of the embodiment illustrated in FIGS. 59–62, an intermediate array 882 of tethering cords 870 extends between the main section 850 of the cannula and the inner side surface of the flexible wall or bladder 852. In addition, an axially inner array 884 of tethering cords 870 extends between the inner side surface of the bladder or flexible wall and the main section 850 of the cannula.

The three arrays 880, 882, and 884 of tethering cords 870 used to restrain outward movement of the flexible wall or bladder 852 in the embodiment of the invention illustrated in FIGS. 59–62 are effective to cause the extended flexible wall 852 to form an inflated structure having a generally conical configuration.

Figure 63:
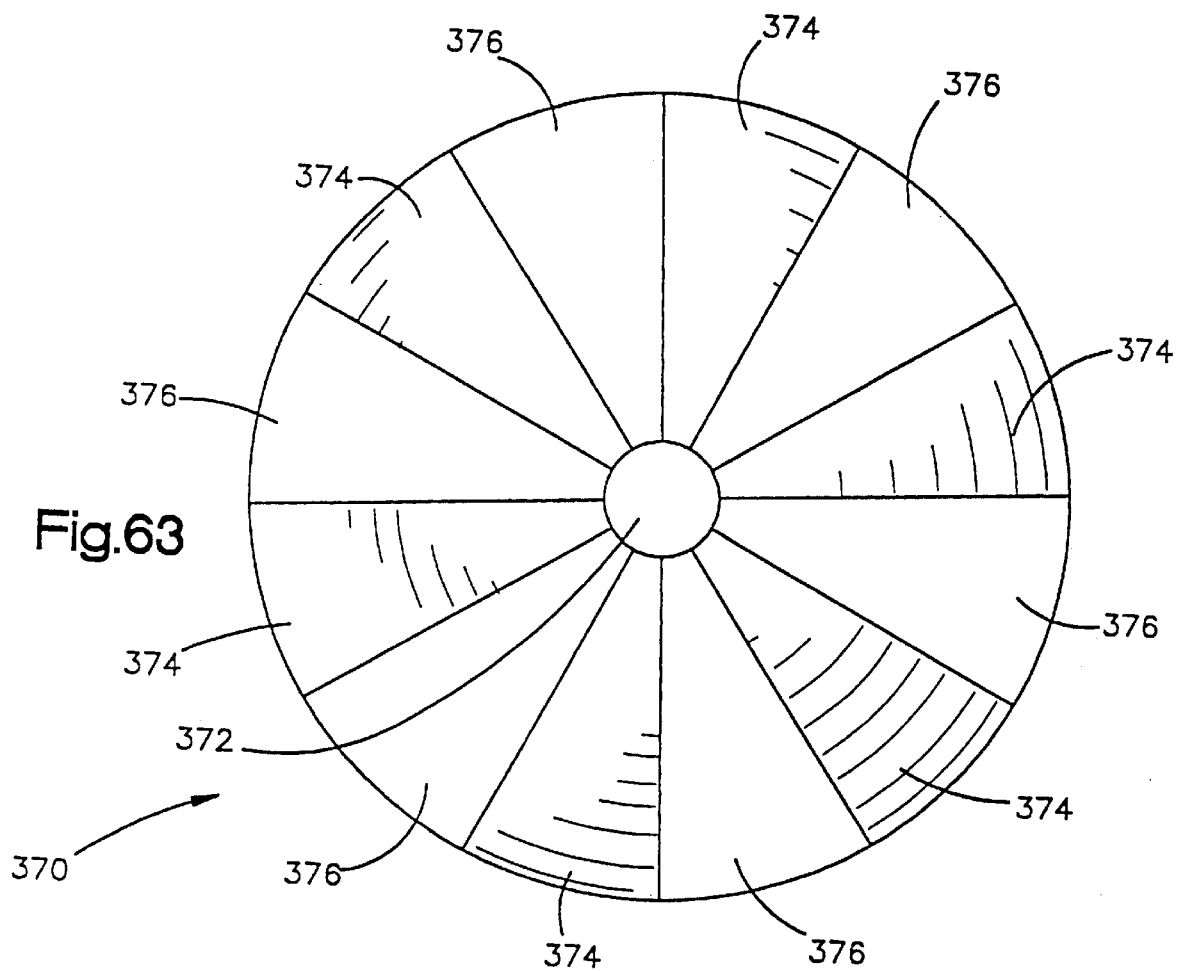
FIG. 63 illustrates an expanded bladder having adjoining portions with different material characteristics.

FIG. 63 illustrates an expanding bladder 370 having adjoining portions with different material characteristics. The device is shown in end view as disposed circumferentially around a cannula 372. Alternate portions 374 of the device are made of a first material having a first set of material characteristics, while the interfitted portions 376 are made of a second material having a second set of material characteristics. For example, one material may have a lower modulus of elasticity and the other a higher modulus of elasticity. One may be thicker and the other thinner. One may be elastomeric and the other not. Other combinations are possible. The portions may be bonded together with adhesive, may be heat-sealed together, or may be solvent sealed. One portion can be made of metal. PVC is also a suitable material.

Upon the introduction of fluid under pressure into the expanding device 370, the portions 374 and 376 expand or move at different rates or into different shapes. The adjoining of different materials can be used to control the expanded shape of the device 370.

Figure 64:
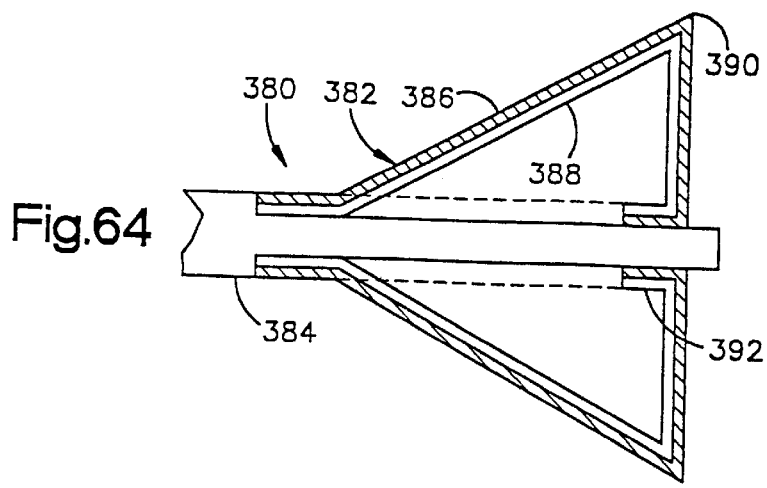
FIG. 64 illustrates an expanding device having an expanding bladder made of a plurality of materials laminated together.

FIG. 64 illustrates an expanding device 380 having an expanding bladder 382 made of a plurality of materials laminated together. The expanding portion 382 is mounted on a stalk or cannula 384. The bladder 382 includes an outer layer 386 of a first material laminated to an inner layer 388 of a second material. Again, the layers may have differing material characteristics—perhaps polymers with specific properties bonded together. For example, the layer 386 may be of a different durometer from the material of the layer 388. One of the layers may provide structural support while the other provides fluid sealing capabilities. One layer may provide puncture resistance while the other provides expansion shape control. These are some of the many properties available with such laminated structures.

It should also be noted that the expandable bladder 382 has an expanded dimension many times greater than its unexpanded dimension as illustrated in dashed lines in FIG. 64. This is illustrative of the large degree of expansion which the expandable bladders of the present invention are able to generate. For example, expandable bladders in accordance with the present invention have been built having expansion rates of approximately 700% as compared to the unexpanded diameter.

Figure 65A:
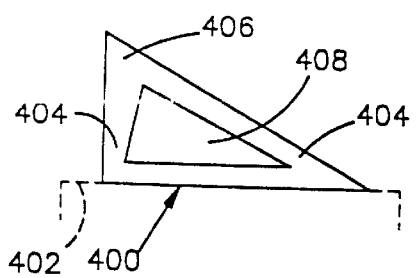
FIGS. 65A–65C illustrate triangular-shaped expanding portions.

FIG. 65A illustrates a triangular shaped expanding element 400 fixed to a supporting device indicated at 402. The expanding element 400 has relatively thin walled portions 404 and a relatively thick wall portion 406. Upon the introduction of fluid under pressure into the volume 408 defined by the bladder 400, the relatively thin walled portions 404 are stretched to a greater extent than the relatively thick walled portion 406. In the similar expanding segment 410 (FIG. 65B), a fiber 412 is embedded in the elastomeric material of the expanding segment to control and limit its expansion. Again, in the similar expanding segment 414 illustrated in FIG. 65C, a fiber mesh 416 is embedded in the elastomeric material of the expanding segment to strengthen it and to control its expansion.

Figure 65B:
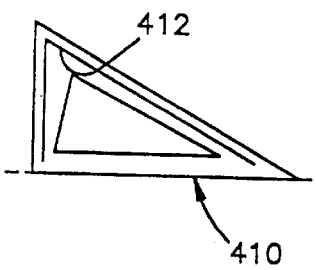
Figure 65C:
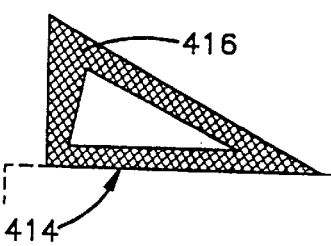
Figure 66A:
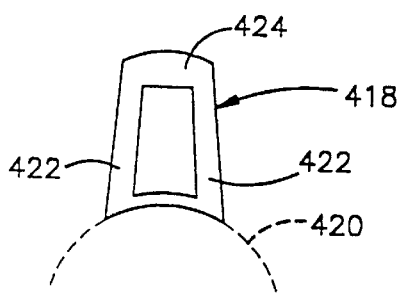
FIGS. 66A–66C illustrate trapezoidal-shaped expanding portions.
Figure 66B:
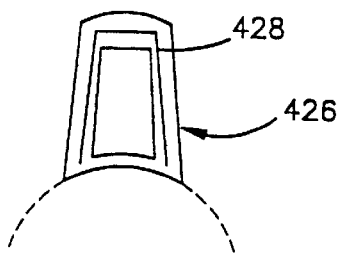
Figure 66C:
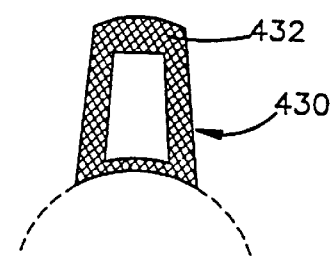

The expanding segments illustrated in FIGS. 66A, 66B, and 66C are similar to FIGS. 65A–65C in structural composition but are trapezoidal shaped rather than triangular shaped. FIG. 66A illustrates an expanding segment 418 connected with a support member 420. The segment 418 includes relatively thin walled portions 422 and a relatively thick walled portion 424. Upon the introduction of fluid under pressure into the volume defined by the expanding portion 418, the relatively thin walled portions 422 stretch to a greater extent than the relatively thick walled portion 4246 whereby the relatively thick walled portion 424 moves radially outwardly to a greater extent. The expanding segment 426 (FIG. 66B) includes an embedded reinforcing fiber 428 for expansion control purposes. The expanding segment 430 (FIG. 66C) includes an embedded fiber mesh 432 for structural support and expansion control purposes. The structural compositions and uses of embedded fibers and fiber meshes illustrated in FIGS. 65 and 66 are merely illustrative of the various ways in which fibers embedded in the elastomeric material of an expanding medical device can be used to control the expansion thereof.

Figure 67A:
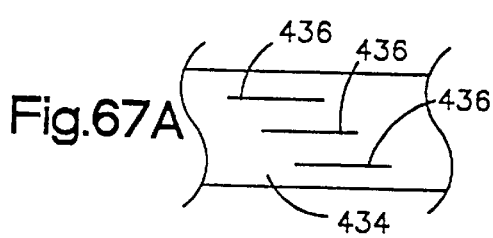
FIGS. 67A–67C illustrate the use of overlapping and/or incomplete fibers for expansion control.
Figure 67B:
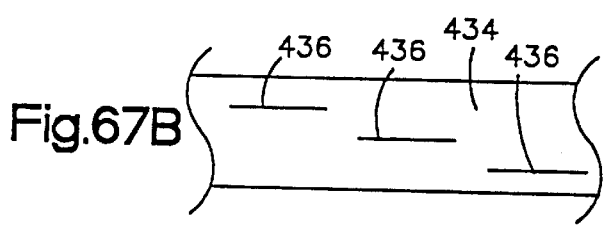
Figure 67C:
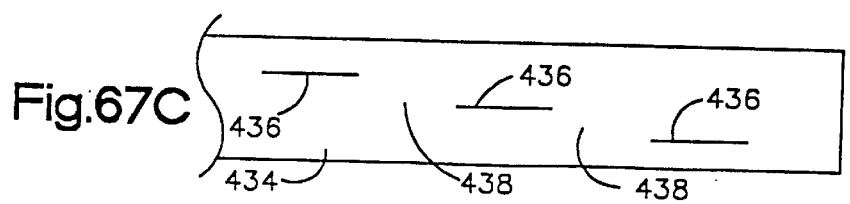

FIGS. 67A–67C illustrate the use of overlapping and/or incomplete reinforcing fibers for expansion control. A stretchable elastomeric material 434 (FIG. 67A) has a plurality of fibers or other reinforcing elements 436 embedded therein. As the stretchable material 434 is elongated, the elastomeric material in the stretch zones 438 (FIG. 67C) between the fiber portions 436 stretches to a greater extent than the material immediately around the fibers 436. Further, the embedded fibers resist transverse expansion of the elastomeric material while encouraging longitudinal expansion as shown. These drawings are merely illustrative of the use of the concept of overlapping fibers with stretch zones to control expansion rates of an elastomeric material used in an expanding medical device such as a cannula or catheter. The present invention contemplates other such arrangements of fibers or reinforcing elements in the elastomeric materials.

For example, FIGS. 68–70 illustrates a bladder retractor 440 fixed to a cannula 442. A plurality of circumferentially extending reinforcing fibers 444 are embedded in an elastomeric matrix material 446. In addition, a plurality of tethering cords 448 extend radially between the cannula 442 and the elastomeric material 446 to limit the radially outwardly expansion. As can be seen in FIG. 70, the reinforcing fibers 444 are not complete but rather are broken fibers extending circumferentially within the matrix material 446 to define stretch zones between them. Alternatively, the reinforcing fibers may be complete, as illustrated in FIGS. 71 and 72. In the retractor 450 illustrated in FIGS. 71 and 72, a plurality of complete circumferentially extending reinforcing fibers 452 are embedded in the matrix material 454. The retractor 456 illustrated in FIGS. 73 and 74 includes a plurality of longitudinally extending incomplete reinforcing fibers 458 embedded in the matrix material 460. The retractor 462 illustrated in FIGS. 75 and 76 includes a plurality of longitudinally extending complete reinforcing fibers 464 embedded in an elastomeric matrix material 466. Again, the invention contemplates other such configurations of reinforcing fibers embedded in matrix materials, and is not limited to those shown.

Figure 77:
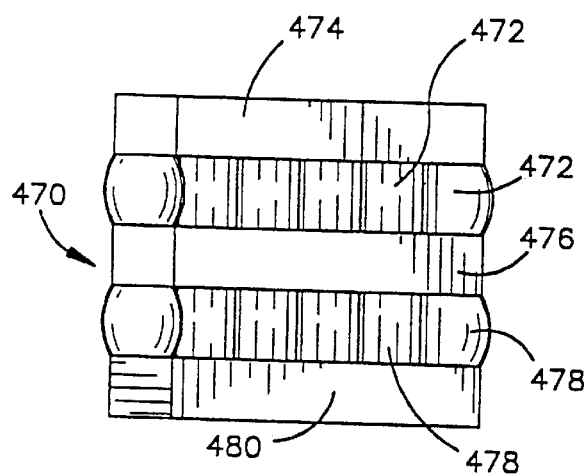
FIGS. 77–79 illustrate a structural unit comprising a series of expandable bladders laminated together.
Figure 78:
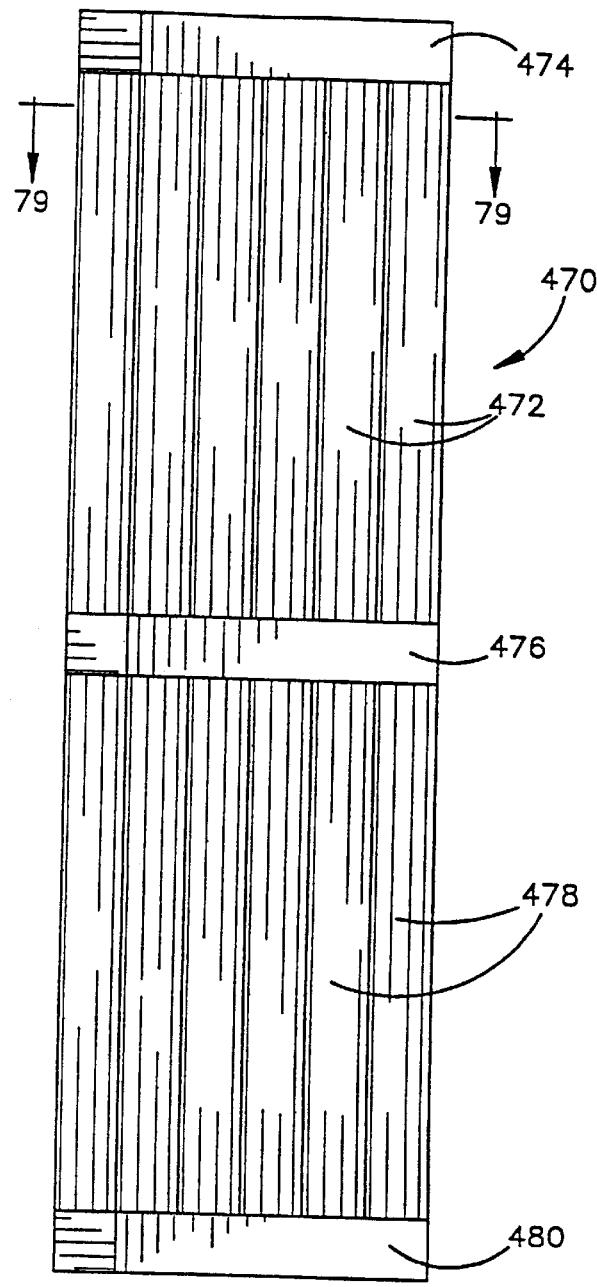
Figure 79:
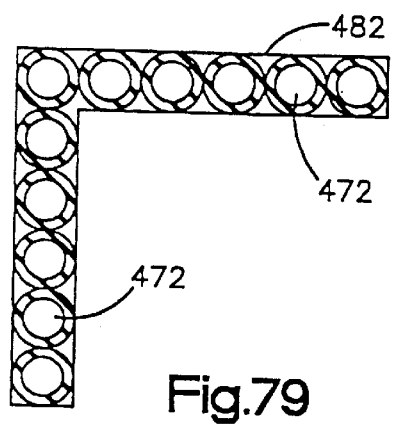

FIGS. 77–79 illustrate a series of expandable bladders laminated together to define a structural unit 470. A series of upper longitudinally extendable bladders 472 have their ends fixed between an upper member 474 and a central member 476. A series of lower longitudinally extending bladders 478 have their ends fixed between the central member 476 and a lower member 480. A covering or retainer 482 (FIG. 79) may enclose all of the units. Upon the introduction of fluid under pressure, the bladders 472 and 478 expand longitudinally from the condition illustrated in FIG. 77 to the condition illustrated in FIG. 78. When the bladders 472 and 478 are fully inflated as illustrated in FIG. 54, they define, together with the members 474, 476 and 480 and the retainer 482, a rigid structural unit. This type of laminated bladder construction will find many suitable uses. It should be understood that other configurations of bladders laminated together are contemplated and are within the scope of the invention.

From the above description of the invention, those skilled in the art will perceive improvements, changes and modifications in the invention. Such improvements, changes and modifications within the skill of the art are intended to be covered by the appended claims.

I claim:

1. A method of providing surgical access through an incision in the body and for maintaining a seal with the incision, said method comprising:

providing a tubular member having proximal and distal ends, said tubular member having a bore extending therethrough and an outer wall, said outer wall being expandable for contacting the incision and making a seal therewith, an inflatable member within said bore of said tubular member, said inflatable member capable of assuming a deflated state where said bore in said tubular member is at least partially unobstructed and an inflated state where said inflatable member substantially fills said bore to seal said bore, and a fluid passageway in communication with said inflatable member;

inserting said distal end of said tubular member through the incision with said proximal end remaining outside said body and said outer wall positioned at the location of the incision;

inflating said inflatable member such that the inflatable member expands across said bore and seals said bore; and expanding said outer wall into contact with the incision.

2. The method of claim 1 wherein said tubular member is flexible.

3. The method of claim 2 wherein said tubular member is formed from an elastomeric material.

4. The method of claim 2 wherein said tubular member is a skin seal.

5. The method of claim 2 wherein said tubular member is a cannula.

6. The method of claim 1 wherein said tubular member is a skin seal.

7. The method of claim 1 wherein said tubular member is a cannula.

8. The method of claim 1 wherein said inflatable member is substantially toroidal in shape.

9. The method of claim 1 further comprising a surgical instrument inserted through said central opening and wherein said inflatable member is capable of forming a substantially fluid-tight seal around said surgical instrument when inflated.

10. The method of claim 1 wherein said fluid passageway comprises a lumen formed in said wall of said tubular member.

11. The method of claim 1 wherein said inflatable member in its deflated state allows a surgical instrument to pass freely through said central opening and wherein said inflatable member in said inflated state forms a substantially fluid-tight seal around the surgical instrument.

12. The method of claim 11 wherein said inflatable member is formed of an elastomeric material.

13. The method of claim 11 wherein said inflatable member is formed of a nonelastomeric material.

14. The method of claim 1 wherein said tubular member has an inner wall and said inflatable member is formed by a portion of said inner wall, said inflatable member having an inflatable space formed in said tubular member between said inner wall and said outer wall.

15. The method of claim 1 wherein said outer wall comprises a second inflatable member.

16. The method of claim 1 wherein said tubular member has an elliptical cross-section.

17. A method of providing surgical access through an incision in the body and for maintaining a seal with the incision, said method comprising:

providing a tubular member having proximal and distal ends;

said tubular member having a bore extending therethrough, and an outer wall having an expandable portion for contacting the incision and for making a seal therewith; and an inflatable member within said tubular member, said inflatable member capable of assuming a deflated state where said bore in said tubular member is at least partially unobstructed and an inflated state where said inflatable member substantially fills said bore to seal said bore;

inserting said distal end of said tubular member through the incision with said proximal end remaining outside said body and said outer wall positioned at the location of the incision;

inflating said inflatable member across said bore of said tubular member to substantially seal said bore;

expanding said expandable portion of said outer wall into contact with the incision;

deflating said inflatable member;

inserting a surgical instrument through said bore, and inflating said inflatable member thereby sealing around said surgical instrument.

18. The method of claim 17 wherein said tubular member is flexible.

19. The method of claim 18 wherein said tubular member is a skin seal.

20. The method of claim 18 wherein said tubular member is a cannula.

21. The method of claim 17 wherein said tubular member is a skin seal.

22. The method of claim 17 wherein said tubular member is a cannula.

23. The method of claim 17 wherein said inflatable member is substantially toroidal in shape.

24. The method of claim 17 wherein said inflatable member is formed of an elastomeric material.

25. The method of claim 17 wherein said tubular member has an inner wall and said inflatable member is formed in said tubular member between said inner wall and said outer wall.

26. The method of claim 17 further comprising the step of expanding said expandable portion of said outer wall to seal the incision.

27. The method of claim 17 wherein said tubular member has an elliptical cross-section.

28. A method of providing a working passage through an incision in a body comprising the following steps:

providing a cannula comprising a housing having proximal and distal ends, a longitudinal lumen extending the length of the cannula, an expandable portion disposed in an outer wall of said cannula, and an inflatable member disposed within said lumen of said housing, said inflatable member having a deflated state wherein said lumen is at least partially unobstructed and an inflated state wherein said inflatable member expands across said lumen to substantially fill and seal said lumen;

inserting said distal end of said cannula through the incision with said proximal end remaining outside said body and said expandable portion positioned at the location of the incision;

expanding the expandable portion into contact with the incision; and inflating said inflatable member such that the inflatable member expands across said lumen and seals said lumen.

29. The method of claim 28 wherein said housing is flexible.

30. The method of claim 28 wherein said housing is substantially rigid.

31. The method of claim 28 further comprising the step of inserting a surgical instrument through said lumen, inflating said inflatable member to form a seal around said instrument.

32. A method of providing surgical access through an incision in the body and for maintaining a seal with the incision, said method comprising:

providing a cannula comprising a tubular member having proximal and distal ends, a longitudinal lumen extending the length of the cannula, an inflatable inner wall portion and an expandable outer wall portion disposed along said tubular member, an annular space disposed between said inflatable inner wall portion and said expandable outer wall portion, and a fluid passageway extending along said tubular member to said annular space;

inserting said distal end of said cannula through the incision with said proximal end remaining outside the body and said inflatable inner wall portion and said expandable outer wall portion positioned within the incision;

expanding said expandable outer wall portion into contact with the incision to seal the incision; and inflating said inflatable inner wall portion to expand it across said lumen to substantially fill and seal said lumen.

33. The method of claim 32 wherein said tubular member is flexible.

34. The method of claim 32 wherein said tubular member is substantially rigid.

35. The method of claim 32 further comprising the step of inserting a surgical instrument through said lumen, inflating said inflatable inner wall portion to form a seal around said instrument.

* * * * *